United States Patent
Yonekawa

(10) Patent No.: US 9,186,118 B2
(45) Date of Patent: Nov. 17, 2015

(54) RADIOGRAPHIC IMAGING SYSTEM

(75) Inventor: Hisashi Yonekawa, Hachioji (JP)

(73) Assignee: KONICA MINOLTA, INC. (JP)

( * ) Notice: Subject to any disclaimer, the term of this patent is extended or adjusted under 35 U.S.C. 154(b) by 245 days.

(21) Appl. No.: 13/502,287

(22) PCT Filed: Aug. 17, 2010

(86) PCT No.: PCT/JP2010/063858
§ 371 (c)(1),
(2), (4) Date: Apr. 16, 2012

(87) PCT Pub. No.: WO2011/048868
PCT Pub. Date: Apr. 28, 2011

(65) Prior Publication Data
US 2012/0207278 A1      Aug. 16, 2012

(30) Foreign Application Priority Data
Oct. 20, 2009    (JP) .................................. 2009-241008

(51) Int. Cl.
*H05G 1/64*   (2006.01)
*A61B 6/00*   (2006.01)
*G03B 42/04*  (2006.01)

(52) U.S. Cl.
CPC .............. *A61B 6/465* (2013.01); *A61B 6/4233* (2013.01); *A61B 6/4283* (2013.01);
(Continued)

(58) Field of Classification Search
CPC ...... A61B 6/4494; A61B 6/465; A61B 6/566; A61B 6/4405
USPC ........................................................ 378/98.5
See application file for complete search history.

(56) References Cited

U.S. PATENT DOCUMENTS

2002/0090055 A1   7/2002   Zur et al.
2006/0016998 A1   1/2006   Ohara
(Continued)

FOREIGN PATENT DOCUMENTS

JP    10-206553 A   8/1998
JP    11-113889 A   4/1999
(Continued)

OTHER PUBLICATIONS

Eguchi (WO2008111355). Sep. 18, 2008.*
(Continued)

*Primary Examiner* — David J Makiya
*Assistant Examiner* — Danielle Fox
(74) *Attorney, Agent, or Firm* — Cantor Colburn LLP

(57) ABSTRACT

Disclosed is a radiographic imaging system which is provided with: a plurality of radiographing chambers equipped with a registration device; a console; and a management device for associating and managing the identification information of a portable radiographic imaging device with the identification information of the radiographing chambers. When the identification information of the portable radiographic imaging device is notified by the registration device of a radiographing chamber, the console displays an icon corresponding to the imaging device on a selection screen. When the identification information of the portable radiographic imaging device, as notified by the registration device, is associated with the identification information of another radiographing chamber, the management device discards the association and deletes the icon corresponding to the portable radiographic imaging device from the selection screen of the console, which is associated with said other radiographing chamber.

4 Claims, 14 Drawing Sheets

(52) U.S. Cl.
CPC ............ *A61B 6/4405* (2013.01); *A61B 6/4411* (2013.01); *A61B 6/4494* (2013.01); *A61B 6/547* (2013.01); *A61B 6/566* (2013.01); *G03B 42/04* (2013.01)

(56) References Cited

U.S. PATENT DOCUMENTS

| | | | |
|---|---|---|---|
| 2006/0054822 A1 | 3/2006 | Tsuchino | |
| 2009/0022276 A1 | 1/2009 | Ohara | |
| 2009/0028295 A1 | 1/2009 | Ohta et al. | |
| 2012/0286167 A1* | 11/2012 | Eguchi | 250/393 |

FOREIGN PATENT DOCUMENTS

| | | |
|---|---|---|
| JP | 2002-156717 A | 5/2002 |
| JP | 2002-336225 A | 11/2002 |
| JP | 2005-114944 A | 4/2005 |
| JP | 2005-121783 A | 5/2005 |
| JP | 2006-247141 A | 9/2006 |
| JP | 2009-45435 A | 3/2009 |
| JP | 2009204671 A | 9/2009 |
| WO | 2006/109551 A1 | 10/2006 |
| WO | 2008/111355 A1 | 9/2008 |
| WO | 2008111355 A1 | 9/2008 |
| WO | 2009/051017 A1 | 4/2009 |
| WO | 2009047994 A1 | 4/2009 |
| WO | 2009142041 A1 | 11/2009 |

OTHER PUBLICATIONS

International Search Report for International Application No. PCT/JP2010/063858, mailed Nov. 16, 2010, with English translation.
United States Non Final Office Action corresponding to U.S. Appl. No. 14/268,392; Date of Mailing: Apr. 23, 2015.
Japanese Notification of Reasons for Refusal corresponding to Application No. 2014-166278; Date of Mailing: Jun. 9, 2015, with English translation.
Extended European Search Report corresponding to Application No. 10824720.6-1660/2491861 PCT/JP2010/063858; Date of Mailing: Jun. 30, 2015.

* cited by examiner

FIG. 13

| RADIOGRAPHING ORDER ID | PATIENT ID | PATIENT NAME | SEX | AGE | DIAGNOSIS DEPARTMENT | RADIOGRAPHED BODY PART | RADIOGRAPHING DIRECTION |
|---|---|---|---|---|---|---|---|
| 001 | 100085 | A | MALE | 25 | SURGERY | CHEST | SIDE L |
| 002 | 100085 | A | MALE | 25 | SURGERY | CHEST | SIDE R |
| 003 | 100085 | A | MALE | 25 | SURGERY | LEG | L |
| 004 | 100085 | A | MALE | 25 | SURGERY | LEG | R |
| 005 | 100125 | B | FEMALE | 55 | GYNECOLOGY | BREAST | MLO-R |
| 006 | 100125 | B | FEMALE | 55 | GYNECOLOGY | BREAST | MLO-L |
| 007 | 100125 | B | FEMALE | 55 | GYNECOLOGY | BREAST | CC-L |
| 008 | 100125 | B | FEMALE | 55 | GYNECOLOGY | BREAST | CC-R |
| 009 | 100320 | C | MALE | 15 | PLASTIC SURGERY | LEG | L |
| 010 | 100325 | D | MALE | 60 | PLASTIC SURGERY | HAND | L |

FIG. 14

PLEASE INPUT RADIOGRAPHING ORDER INFORMATION FOR SCHEDULED RADIOGRAPHING

| RADIOGRAPHING ORDER ID | PATIENT ID | PATIENT NAME | SEX | AGE | DIAGNOSIS DEPARTMENT | RADIOGRAPHED BODY PART | RADIOGRAPHING DIRECTION |
|---|---|---|---|---|---|---|---|
| 001 | 100085 | A | MALE | 25 | SURGERY | CHEST | SIDE L |
| 002 | 100085 | A | MALE | 25 | SURGERY | CHEST | SIDE R |
| 003 | 100085 | A | MALE | 25 | SURGERY | LEG | L |
| 004 | 100085 | A | MALE | 25 | SURGERY | LEG | R |
| 005 | 100125 | B | FEMALE | 55 | GYNECOLOGY | BREAST | MLO-R |
| 006 | 100125 | B | FEMALE | 55 | GYNECOLOGY | BREAST | MLO-L |
| 007 | 100125 | B | FEMALE | 55 | GYNECOLOGY | BREAST | CC-L |
| 008 | 100125 | B | FEMALE | 55 | GYNECOLOGY | BREAST | CC-R |
| 009 | 100320 | C | MALE | 15 | PLASTIC SURGERY | LEG | L |
| 010 | 100325 | D | MALE | 60 | PLASTIC SURGERY | HAND | L |

DECIDE  RETURN

RADIOGRAPHIC IMAGING SYSTEM

CROSS REFERENCE TO RELATED APPLICATIONS

This is a U.S. national stage of application No. PCT/JP2010/063858, filed on 17 Aug. 2010. Priority under 35 U.S.C. §119(a) and 35 U.S.C. §365(b) is claimed from Japanese Application No. 2009-241008, filed 20 Oct. 2009, the disclosure of which are also incorporated herein by reference.

FIELD OF THE INVENTION

The present invention relates to a radiographic imaging system, particularly to a radiographic imaging system provided with a plurality of radiographing chambers.

BACKGROUND

A radiographic image represented by an X-ray image and captured by using radiation has found widespread application for the purpose of disease diagnosis and others. The radiographic image for medical treatment was captured using a screen film in the conventional method. However, the realized digitization of a radiographic image in recent years has allowed a CR (Computed Radiography) apparatus to come into widespread use, for example, wherein the radiation having passed through a subject is accumulated on a stimulable phosphor sheet in which a stimulable phosphor layer is formed. The stimulable phosphor sheet is then scanned by a beam of laser, so that the stimulable light emitted from the stimulable phosphor sheet is subjected to photoelectric conversion, whereby image data is obtained.

When a CR device is used for radiographic imaging, the cassette (e.g., Patent Literatures 1 through 3, hereinafter referred to as "CR cassette") incorporating such a recording medium as a screen film or stimulable phosphor sheet is often kept loaded on the bucky device or the like. This CR cassette is often designed and manufactured according to the JIS-specified size for the conventional screen film cassette so that this CR cassette can be used after being mounted on the existing bucky device introduced for use with the conventional screen film cassette mounted thereon.

When the CR cassette is designed and manufactured in this manner, the size of the screen film cassette is made uniform with that of the CR cassette, and effective use of the existing facility for the screen film can be ensured with the interchangeability maintained between the two. This arrangement also allows the image data to be digitalized.

The radiographic image capturing devices for medical treatment developed in recent years include a FPD (Flat Panel Detector) which is a detector for acquiring digital image data by detecting the radiation having been applied, namely, a radiographic imaging device. This is further developed into a portable radiographic imaging device having sizes interchangeable with a CR cassette wherein the aforementioned FPD is incorporated in a housing (Patent Literature 4).

Since the FPD cassette having a size interchangeable with such a CR cassette is portable, one FPD cassette is assumed to be used commonly in various radiographing chambers. Thus, the systems disclosed so far includes a system in which, when used in combination with the X-ray tube and bucky device arranged in each of the radiographing chambers, the correction optimum to each combination is applied to the image data obtained from the FPD cassette, whereby uniform image data is provided in the final phase (Patent Literatures 5 and 6).

Patent Literature 7 discloses a specific method for combination detection in which an FPD cassette is equipped with a fixed detecting section and mark detecting section, and, when the FPD cassette is loaded on the cassette holder of the bucky device, and the fixed detecting section of the FPD cassette has come in contact with the fixed portion provided on the bucky device, the mark detecting section of the FPD cassette reads the mark of the cassette holder. Then the ID information of the bucky device recorded in the mark and the ID information of the FPD cassette are sent to an external device through a cable so as to select an image processing (correction) parameter best suited to the radiographing.

PRIOR TECHNOLOGICAL LITERATURE

Patent Literature

Patent Literature 1: Unexamined Japanese Patent Application Publication No. 2005-121783
Patent Literature 2: Unexamined Japanese Patent Application Publication No. 2005-114944
Patent Literature 3: Unexamined Japanese Patent Application Publication No. 2002-156717
Patent Literature 4: Official Gazette of International Publication No. 2009/051017 (booklet)
Patent Literature 5: Unexamined Japanese Patent Application Publication No. Hei 10(1998)-206553
Patent Literature 6: Unexamined Japanese Patent Application Publication No. Hei 11(1999)-113889
Patent Literature 7: Unexamined Japanese Patent Application Publication No. 2002-336225

SUMMARY OF THE INVENTION

Problems to be Solved by the Invention

However, many of the existing bucky devices loaded with a CR cassette are not provided with the aforementioned fixed portion or mark. Further, many of these devices are not equipped with a cable for exchange of information with an external device. Accordingly, it is considered that modification is made in such a way that the existing bucky device is provided with a fixed portion or a mark so that a mark can be read after the FPD cassette has been loaded, or a cable is connected to permit exchange of information with an external device to ensure that the technique described in Patent Literature 7 is applicable. However, this requires a large modification cost.

As will be described later, the advantage is that the FPD cassette can be inserted, for example, between the patient and bed for radiographing in an independent state, without the FPD cassette loaded onto a bucky device. However, independent use of the FPD cassette may cause a system failure since there is no ID information of the bucky device.

In view of the problems described above, it is an object of the present invention to provide a radiographic imaging system provided with a plurality of radiographing chambers wherein, when a portable radiographic imaging device (FPD cassette) is used commonly in each of the radiographing chambers, accurate management is made to identify the chamber where the portable radiographic imaging device is located, so as to prevent a system failure from occurring, and to ensure appropriate operation of the aforementioned radiographic imaging system.

Means for Solving the Problems

To solve at least one of the aforementioned problems, a radiographic imaging system reflecting one aspect of the present invention includes:

a portable radiographic imaging device which can be used in common in a plurality of radiographing chambers;

at least one console which has a display section, and which sets radiographing order information including information on a patient as a subject of radiographing and a condition of radiographing, and which associates the radiographing order information with image data captured based on the radiographing order information;

a management device which associates identification information of the portable radiographic imaging device with identification information of a radiographing chamber, and manages to know where the portable radiographic imaging device is located among the plurality of radiographing chambers; and a registration device which is installed in each of the plurality of radiographing chambers and which reads and outputs the identification information of the portable radiographic imaging device and the console is associated with one of the plurality of radiographing chambers selectively at a time of radiographing or in advance, and, when the identification information of the portable radiographic imaging device outputted from the registration device provided in the associated one of the plurality of radiographing chambers has been notified to the console, the console causes the display section to display an icon corresponding to the portable radiographic imaging device thereon, and the management device, when notified of the identification information of the portable radiographic imaging device outputted from the registration device, stores the identification information of the radiographing chamber provided with the registration device and the identification information of the portable radiographic imaging device after being associated with each other, and, if the identification information of the portable radiographic imaging device has been associated with the identification information of another radiographing chamber, discards the association therebetween and deletes the icon corresponding to the portable radiographic imaging device from the display section of the console associated with the other radiographing chamber.

Effects of the Invention

In the type of the radiographic imaging systems of the embodiments of the present invention, when the identification information of a radiographic imaging device has been notified from the registration device installed in a radiographing chamber, the management device stores the identification information of the radiographing chamber and the identification information of the radiographic imaging device by associating them with each other. If the identification information of the radiographic imaging device has been associated with the identification information of another radiographing chamber, the management device discards the association between the identification information of another radiographing chamber and the identification information of the radiographic imaging device. Thus, in a radiographic imaging device equipped with a plurality of radiographing chambers, the management device ensures accurate management of the identification of a radiographing chamber where a radiographic imaging device is currently located.

When the identification information of the radiographic imaging device has been notified from a registration device installed in the radiographing chamber, the console displays the icon corresponding to the radiographic imaging device on the selection screen corresponding to the radiographing chamber provided with the registration device of the display section. At the same time, when the identification information of the radiographic imaging device has been notified from a registration device of another radiographing chamber, the management device deletes the icon corresponding to the radiographic imaging device from the selection screen associated with the original radiographing chamber where the radiographic imaging device was previously located on the display section of the console. This completely solves the problem of failing to identify the current position of a radiographic imaging device, despite the presence of this radiographic imaging device in the radiographing chamber, or keeping an icon corresponding to the radiographic imaging device to be displayed on the selection screen associated with the radiographing chamber on the display section of the console, despite this absence of the radiographic imaging device in the radiographing chamber. Thus, appropriate operation of the radiographic imaging system is ensured.

BRIEF DESCRIPTION OF THE DRAWINGS

FIG. 13 is a drawing illustrating an example of the radiographing order information.

FIG. 14 is a drawing illustrating an example of the selection screen displaying the radiographing order information displayed on the display section of the console.

MODE TO CARRY OUT THE INVENTION

The following describes the embodiment of the radiographic imaging system of the present invention with reference to drawings, without the present invention being restricted to the illustrated examples.

Figure 1:
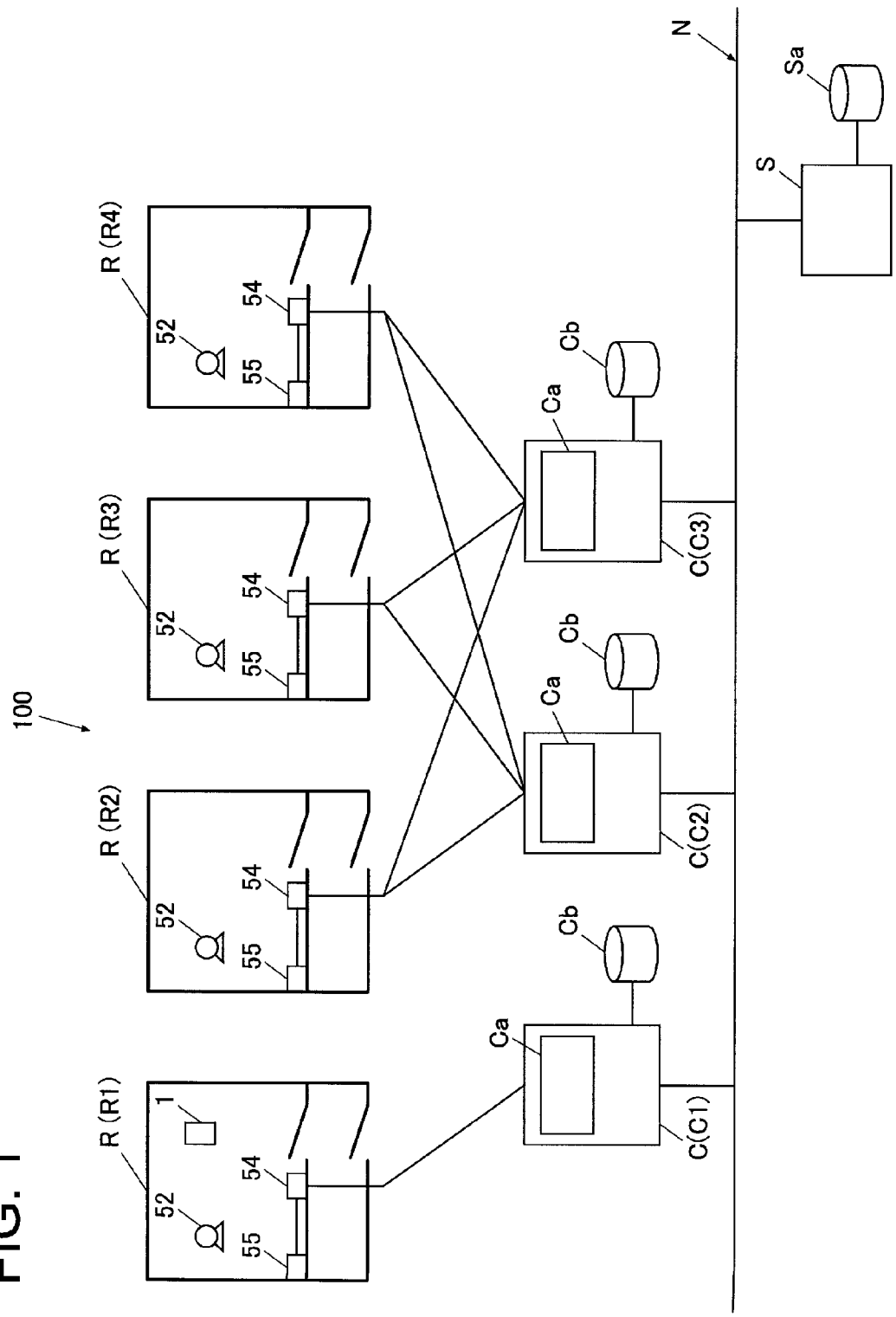
FIG. 1 is a drawing representing an overall structure of a radiographic imaging system of the present invention.

The radiographic imaging system 100 of the present embodiment is a system for radiographic imaging assumed to be conducted in a hospital or a doctor's office. As shown in FIG. 1, a plurality of radiographing chambers R (R1 through R4) and a plurality of consoles C (C1 through C3) are connected in a prescribed manner. A plurality of consoles C (C1 through C3) and a management device S composed of a server and others for managing the information inside the radiographic imaging system 100 are connected via the network N.

It is also possible to design such a structure that a HIS (Hospital Information System) or RIS (Radiology Information System) is connected to the network N, although not illustrated. Further, it is also possible to connect an imager capable of allowing a radiation image to be recorded on the image-recording medium such as a film, and to be outputted, based on the image data outputted from the console C.

Figure 2:
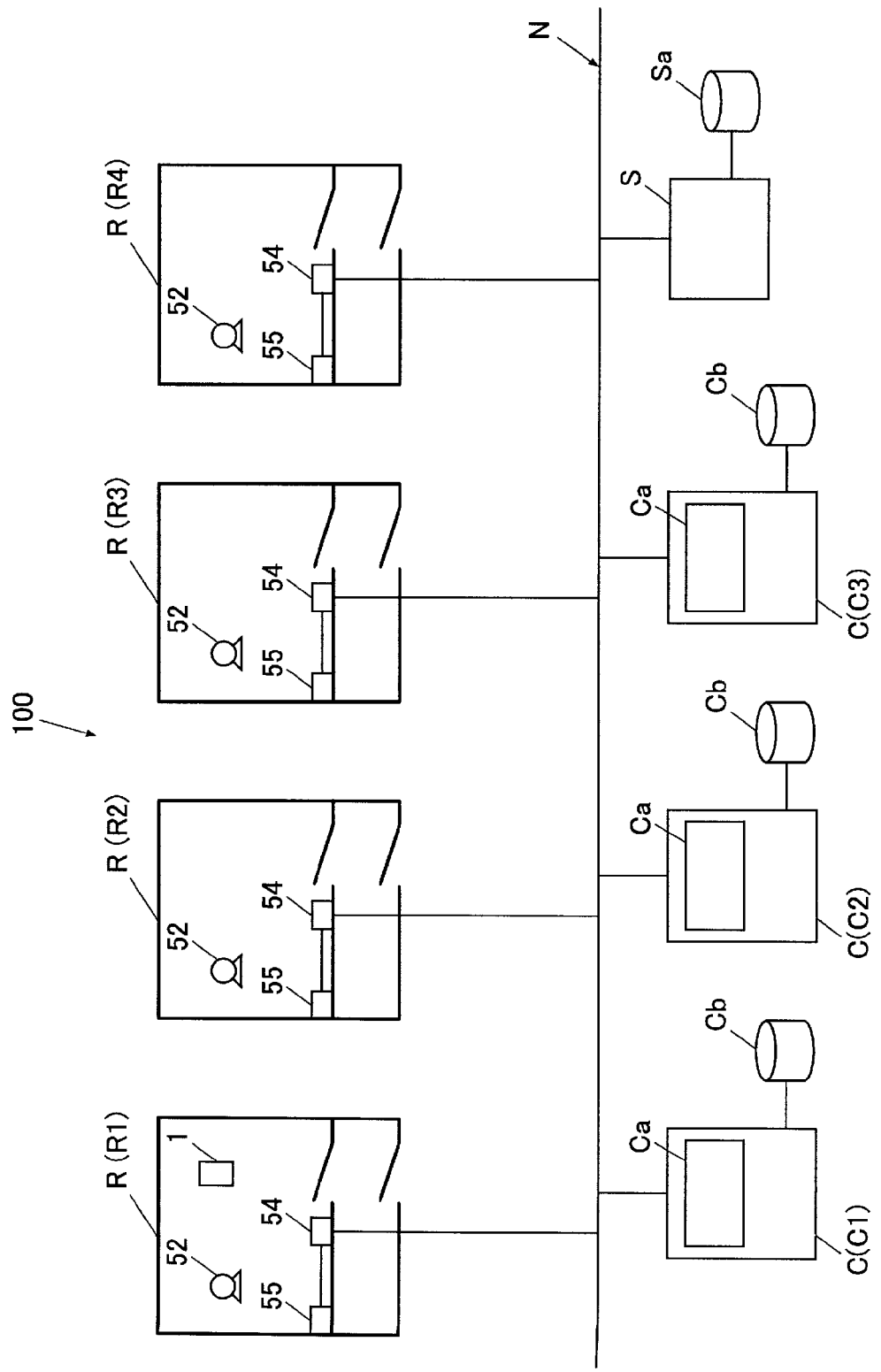
FIG. 2 is a drawing representing another overall structure of the radiographic imaging system of the present invention.

Without being restricted to the example illustrated in FIG. 1, the structure of the radiographic imaging system 100 can be so configured that a plurality of radiographing chambers R (R1 through R4), a plurality of consoles C (C1 through C3) and a management device S are connected via the network N, for example, as shown in FIG. 2.

In the first place, the following describes the portable radiographic imaging device 1 used for radiographing operation in the radiographic imaging system 100.

In the following description, the portable radiographic imaging device will be written simply as radiographic imaging device. Further, in the following description, the radiographic imaging device 1 will be described as a so-called indirect radiographic imaging device equipped with a scintillator to obtain an electric signal by converting the applied radiation into the electromagnetic wave of other wavelength such as visible light. The present invention is also applicable to the so-called direct radiographic imaging device capable of directly detecting the radiation by a radiation-detecting element, without using the scintillator.

Figure 3:
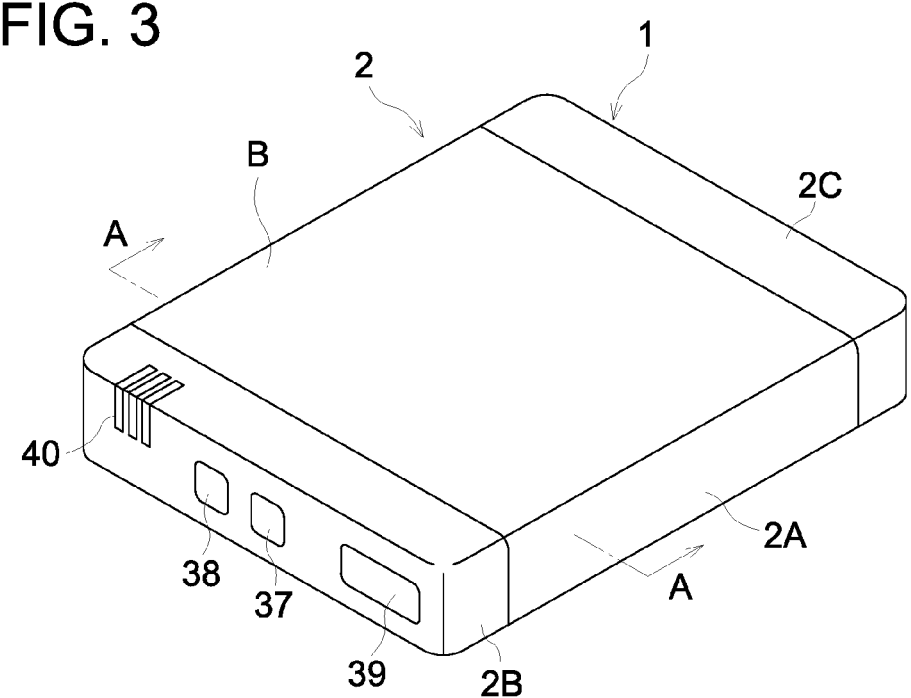
FIG. 3 is an external perspective view of the radiographic imaging device of the present invention.
Figure 4:
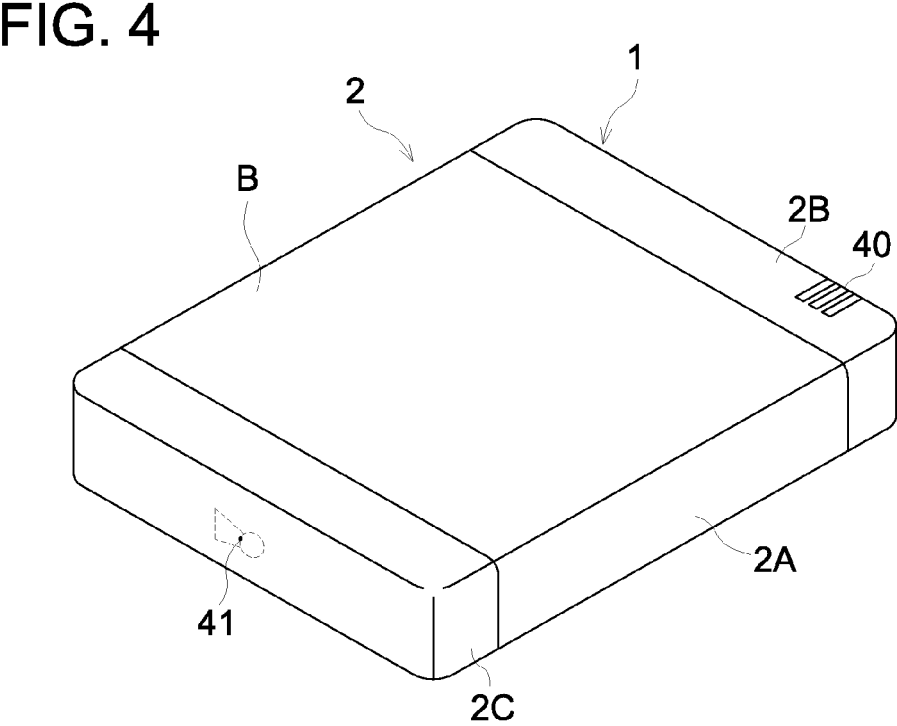
FIG. 4 is an external perspective view of the radiographic imaging device of FIG. 3 as viewed from the opposite side.
Figure 5:
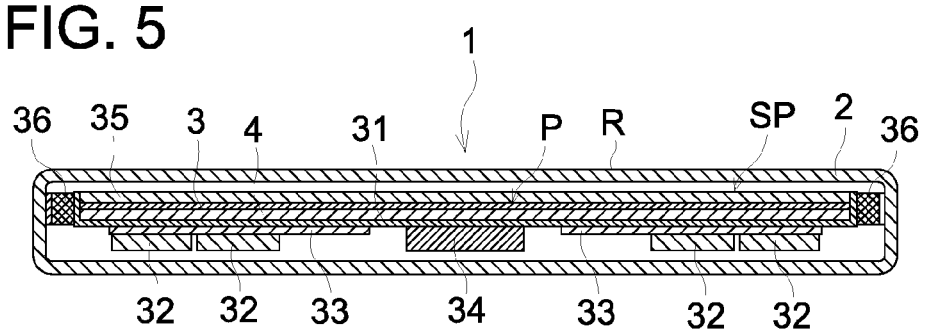
FIG. 5 is a cross sectional view taken along arrow line A-A of FIG. 3.

FIG. 3 is an external perspective view of the radiographic imaging device of the present invention. FIG. 4 is an external perspective view of the radiographic imaging device of FIG. 3 as viewed from the opposite side. FIG. 5 is a cross sectional view taken along arrow line A-A of FIG. 3. The radiographic imaging device 1 is structured in such a way that a sensor panel SP made up of a scintillator 3 and substrate 4 is incorporated in a casing type housing 2 as shown in FIGS. 3 through 5.

As shown in FIGS. 3 and 4, in the present invention, the hollow rectangular tube-shaped housing body 2A having radiation incoming surface B of a casing 2 is made of a carbon plate or plastic material that allows passage of radiation. The casing 2 is formed by blocking the openings on both sides of the housing body 2A by the cover members 2B and 2C. Instead of making the casing 2 in such a monocock structure, the casing 2 can be formed in a so-called lunch box structure made of a frame plate and back plate.

As shown in FIG. 3, the cover member 2B on one side of the casing 2 is provided with a power switch 37; a selector switch 38 to be described later; a connector 39 which is to be linked with the connector 55a of a cradle 55 or connector 51c of a notification device 51b to be described later; and an indicator 40 made of an LED and others capable of indicating the current status of a battery or operating conditions of the radiographic imaging device 1.

Further, as shown in FIG. 4, the cover member 2C on the other side of the casing 2 is provided with an embedded antenna device 41 as a communication device for transmitting the image data to the console C by a wireless method. It is also possible to transmit the image data and others to the console C by a wired method. In this case, a cable is connected to the aforementioned connector 39 to send and receive the data.

Inside the casing 2, as shown in FIG. 5, a support base 31 is arranged on the lower side of the substrate 4 of the sensor panel SP through a lead thin plate or others (not illustrated). A PCB substrate 33 provided with electronic parts 32 and others, and a buffering member 34 are mounted on the support base 31.

In the present embodiment, the radiation incoming surface B of the substrate 4 and scintillator 3 is equipped with glass substrate 35 for protecting these parts. In the present embodiment, a buffering member 36 is provided between the sides of the sensor panel SP and casing 2 to prevent mutual collision.

The scintillator 3 is bonded on the detecting section P (to be described later) of the substrate 4. In the present embodiment, the major component of the scintillator 3 is a fluorophore for example and, upon receipt of the incoming radiation, converts the radiation into the electromagnetic wave having a wavelength of 300 through 800 nm, i.e., the electromagnetic wave including visible light as the main and outputs the resulting electromagnetic wave.

Figure 6:
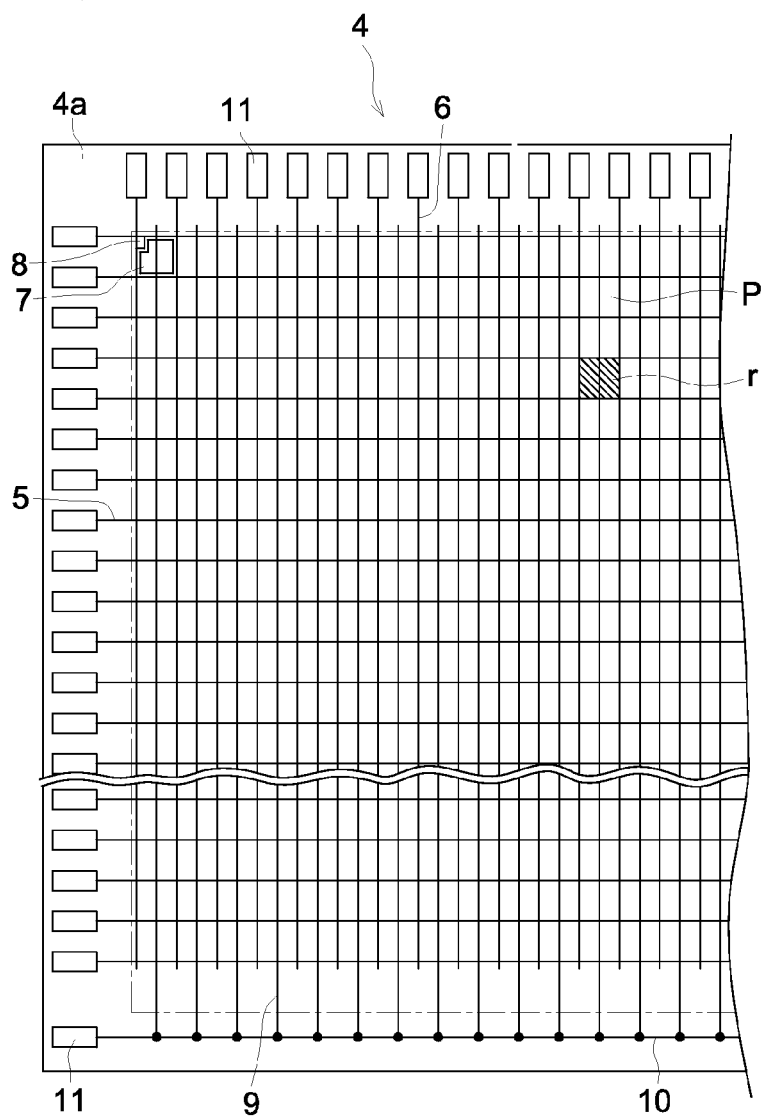
FIG. 6 is a plan view representing the structure of the substrate of the radiographic imaging device.

In the present embodiment, the substrate 4 is made of a glass substrate, and a plurality of scanning lines 5 and signal lines 6 are arranged so as to cross one another on the surface 4a on the side of the substrate 4 opposed to the scintillator 3, as shown in FIG. 6. A radiation-detecting element 7 is provided in each of the small regions "r" partitioned by a plurality of scanning lines 5 and signal lines 6 on the surface 4a of the substrate 4.

As described above, the detecting section P is assumed to be all the areas "r" where a plurality of radiation detecting elements 7 arranged in a two-dimensional array in each small region "r" partitioned by the scanning lines 5 and signal lines 6 are provided, i.e., the region shown by the one-dot chain line in FIG. 6.

Figure 7:
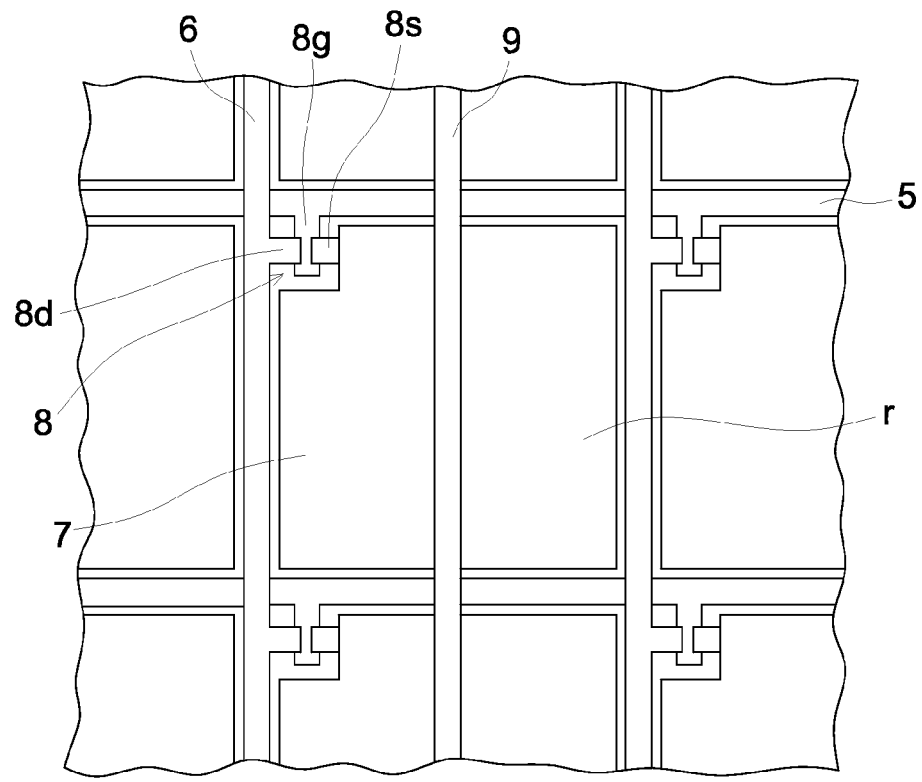
FIG. 7 is an enlarged view showing the structure of the radiation-detecting element formed in the small region on the substrate of FIG. 6 and TFT and others.

In this embodiment, a photodiode is used as the radiation-detecting element 7. In addition, for example, a photo transistor and others can also be used. As shown in FIG. 7 as an enlarged view of FIG. 6, the radiation-detecting element 7 is connected to the source electrode 8s of the TFT 8 as a switching device. Further, the drain electrode 8d of the TFT 8 is connected to the signal line 6.

The TFT 8 is turned on when on-voltage is applied to the gate electrode 8g from a scanning drive device 15 (to be described later) through the scanning line 5 and then the electric charge accumulated in the radiation-detecting element 7 through the source electrode 8s or drain electrode 8d is discharged to the signal line 6. Further, the TFT 8 is turned off when the off-voltage is applied to the gate electrode 8g through the scanning line 5 connected thereto and then discharge of electric charge from the radiation-detecting element 7 to the signal line 6 is suspended and electric charge is kept in the radiation-detecting element 7.

In the present embodiment, as shown in FIG. 7, a bias line 9 is connected to each of a plurality of radiation detecting elements 7 arranged in rows. As shown in FIG. 6, bias lines 9 are bound into one connection wire 10 in positions outside of the detecting section P of the substrate 4.

Figure 8:
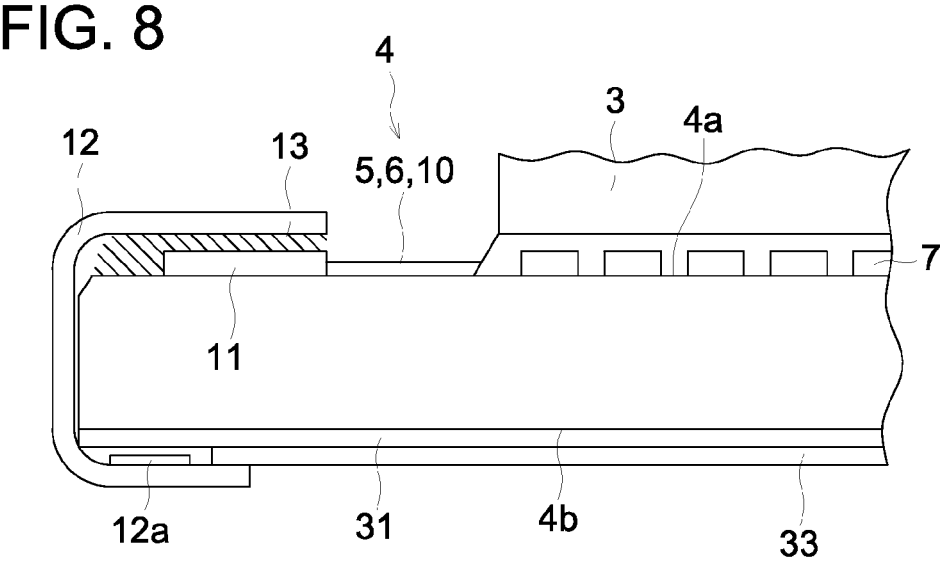
FIG. 8 is a side view showing the substrate on which the COF and PCB are mounted.

The scanning line 5, signal lines 6 and connection wire 10 of the bias line 9 are respectively connected to the input/output terminal (also called a pad) 11 provided near the end of the substrate 4. The input/output terminal 11 is connected with a COF (Chip On Film) 12 with a built-in IC 12a and others through such an anisotropic conductive adhesive material 13 as an anisotropic conductive film or anisotropic conductive paste, as shown in FIG. 8.

The COF 12 is routed to the rear surface 4b of the substrate 4 and is connected to the aforementioned PCB substrate 33 at the rear surface 4b. Thus, the substrate 4 of the sensor panel SP of the radiographic imaging device 1 is formed in the aforementioned manner. In FIG. 8, the electronic parts 32 and others are not illustrated.

Figure 9:
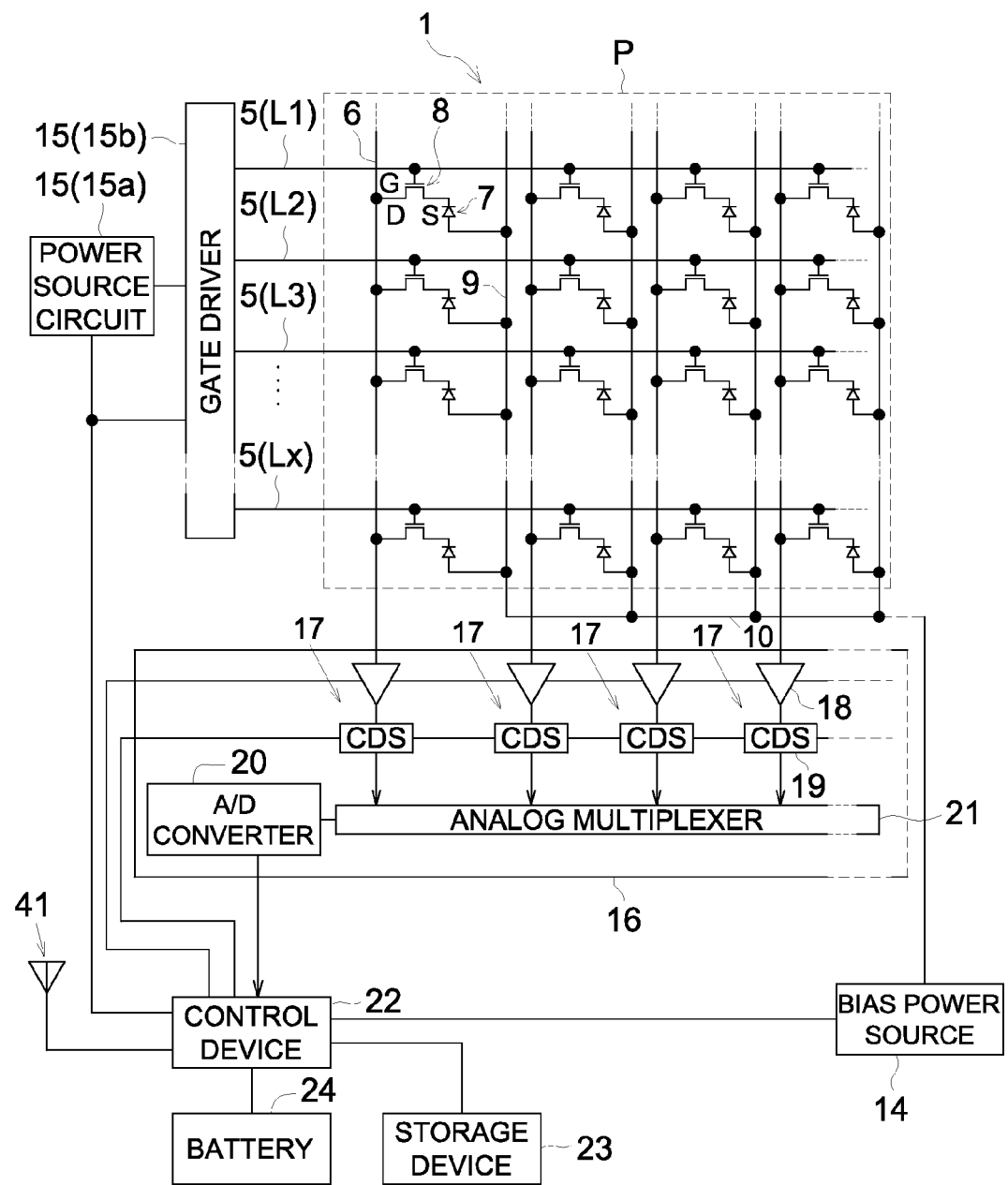
FIG. 9 is a block diagram illustrating the equivalent circuit of the radiographic imaging device.

Referring to FIG. 9, the following describes the circuit structure of the radiographic imaging device 1.

The electrodes on one side of the radiation-detecting element 7 are connected with bias lines 9, respectively. These bias lines 9 are bound into a connection wire 10, which is connected to the bias power source 14. The bias power source 14 applies bias voltage (reverse bias voltage in the present embodiment) to the electrode of the radiation detecting element 7 through the connection wire 10 and bias line 9.

The electrodes on the other side of the radiation detecting elements 7 are connected with the source electrodes 8s ("S" in FIG. 9) of the TFTs 8. The gate electrodes 8g of the TFTs 8 ("G" in FIG. 9) are respectively connected with the lines L1 through Lx of the scanning lines 5 extended from the gate driver 15b of the scanning drive device 15. The drain electrodes 8d ("D" in FIG. 9) of the TFTs 8 are connected with the signal lines 6, respectively.

The scanning drive device 15 is provided with a power circuit 15a for supplying on-voltage or off-voltage to the gate driver 15b, and a gate driver 15b for switching the voltage applied to the lines L1 through Lx of the scanning lines 5 between the on-voltage and off-voltage. As described above, the gate driver 15b switches the voltage applied to the gate electrode 8g of the TFT 8 through the lines L1 through Lx of the scanning lines 5 between the on-voltage and off-voltage, thereby controlling the on/off state of the TFT 8.

The signal lines 6 are connected with the reading circuits 17 formed in the reading IC 16, respectively. The reading circuit 17 includes an amplifier circuit 18, correlated double sampling circuit 19, analog multiplexer 21, and analog-to-digital converter 20.

For example, radiation is applied to the radiographic imaging device 1 through the subject by radiographing operation. The radiation is converted into the electromagnetic wave of another wavelength by the scintillator 3, to be applied to the radiation-detecting element 7 located immediately below. This causes the electric charge (electric signal) to be produced in conformity to the dosage (quantity of light in electromagnetic wave) of the radiation applied by the radiation detecting element 7.

In the process of reading the electric charge from the radiation detecting element 7, a step is taken to turn on the TFT 8 where the on-voltage has been applied to the gate electrode 8g from the gate driver 15b of the scanning drive device 15 through the lines L1 through Lx of the scanning lines 5. Then electric charge is discharged from the radiation detecting element 7 to the signal lines 6. This causes the voltage value to be outputted from the amplifier circuit 18 in conformity to the quantity of electric charge discharged from the radiation detecting element 7. The correlated double sampling circuit 19 applies the process of correlated double sampling to this voltage value and the noise voltage value of the radiation detecting element 7 when the radiation is not applied. Then the image data of an analog value is outputted to the analog multiplexer 21. The image data outputted sequentially from the analog multiplexer 21 is converted into the image data of digital value by the analog-to-digital converter 20, and is outputted to a storage device 23 to be stored therein.

The control device 22 is composed of a CPU (Central Processing Unit), ROM (Read Only Memory), RAM (Random Access Memory), computer with the input/output interface thereof connected to a bus, and FPGA (Field Programmable Gate Array) and others. The control device 22 can be formed of an exclusive control circuit.

The control device 22 controls the operation of each component of the radiographic imaging device 1. The control device 22 controls such processing as resetting of the radiation detecting element 7, reading of the electric charge from the radiation detecting element 7, and dark reading where the dark electric charge accumulated in the radiation detecting element 7 is read, similarly to the process of reading, after the radiographic imaging device 1 has been left, without radiation being applied, to calculate the offset correction value.

The control device 22 is connected with a storage device 23 composed of a DRAM (Dynamic RAM) and others, and a battery 24 for supplying power to the functional portions of the radiographic imaging device 1. Further, the control device 22 is connected with the aforementioned antenna device 41, as well as the aforementioned power switch 37, selector switch 38, connector 39 (FIG. 3) and others, although not illustrated in FIG. 9.

When the selector switch 38 has been pressed by such an operator as a radiographing technician, the control device 22 sends the selection signal showing the selection of the radiographing imaging device itself, to the console C through the antenna device 41. Further, as will be described later, when the connector 39 has been connected to the connector 55a of the cradle 55 in the process of the radiographic imaging device 1 being inserted into the cradle 55, the control device 22 notifies the cradle 55 of the information such as a cassette ID as identification information of the radiographic imaging device 1.

Further, when the connector 39 has been connected with the connector 51c of the notification device 51b (FIG. 10), the control device 22 acquires the information such as bucky ID as identification information of the bucky device 51 from the notification device 51b, and sends both the bucky ID and cassette ID of the radiographic imaging device 1 to the console C.

As described above, in the present embodiment, the radiographic imaging device 1 is considered to be loaded on the bucky device 51 for the screen/film cassette or CR cassette. The radiographic imaging device 1 is formed in size 14"×17" conforming to the JIS standard size for the CR cassette (i.e., the JIS standard size for the conventional screen film The corresponding international standard is IEC 60406). The thickness in the radiation incoming direction is kept in the range from 15 mm+1 mm through 15 mm−2 mm.

However, when a bucky device for the screen/film cassette or CR cassette is not used, the radiographic imaging device 1 need not be formed according to the aforementioned sizes. The radiographic imaging device 1 can be formed in desired sizes or in desired shapes. In this case, a new bucky device formed in conformity to the shape of the radiographic imaging device 1 must be installed to ensure that the radiographic imaging device 1 can be mounted on the bucky device 51.

The following describes the details of the structure of the radiographing chamber R in the radiographic imaging system 100 illustrated in FIGS. 1 and 2.

Figure 10:
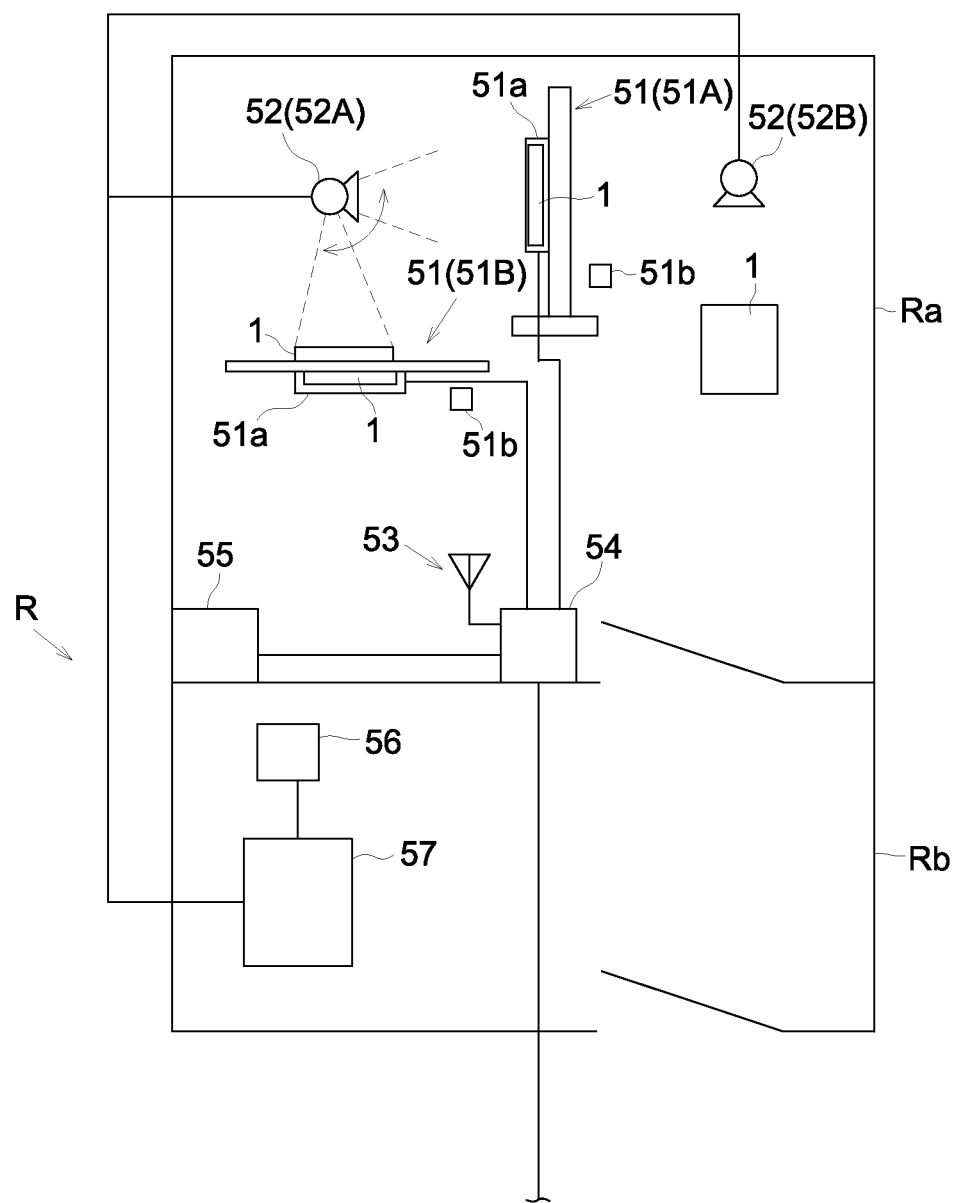
FIG. 10 is a drawing illustrating the structure of the radiographing chamber.

The radiographing chamber R is a room wherein radiographing is conducted by applying radiation to the subject (body part of the patient to be imaged) as part of the patient's body. As shown in FIG. 10, the radiographing chamber R is composed of a so-called radiographing chamber Ra equipped with a radiation generator 52 of the irradiation device for irradiating the subject and provided with measures to prevent leakage of radiation to the outside of the radiographing chamber; and a anteroom (also called an operation room) Rb containing an operation console 57 of the irradiation device to be operated by such an operator as a radiographing technician.

In the present embodiment, the radiographing chamber Ra includes the aforementioned bucky device 51 capable of being loaded with the radiographic imaging device 1, and the radiation generator 52 equipped with an X-ray tube (not illustrated) for generating radiation to be applied to the subject.

As described above, the bucky device 51 is an existing device designed to be employed by mounting a CR cassette on the cassette holding section (cassette holder) 51a. Not only the CR cassette but also the radiographic imaging device 1 can be mounted on the cassette holding section 51a for use. The existing bucky device 51 is not provided with the mark containing the information such as ID information of the fixing section for fixing the radiographic imaging device 1 or the bucky device, as disclosed in Patent Literature 7.

The existing bucky device 51 is provided with a new notification device 51b which sends the information such as bucky ID as identification information of the bucky device 51 to the radiographic imaging device 1 and which contains a power source, a nonvolatile memory for storing bucky ID information and a CPU for communication control (not illustrated). The notification device 51b can be designed for installation on the bucky device 51 or can be mounted close to the bucky device 51.

When the connector 51c of the notification device 51b has been connected to the connector 39 of the radiographic imaging device 1, the notification device 51b sends to the radiographic imaging device 1 the information such as the bucky ID information of the bucky device 51 corresponding to this notification device 51b.

Figure 11:
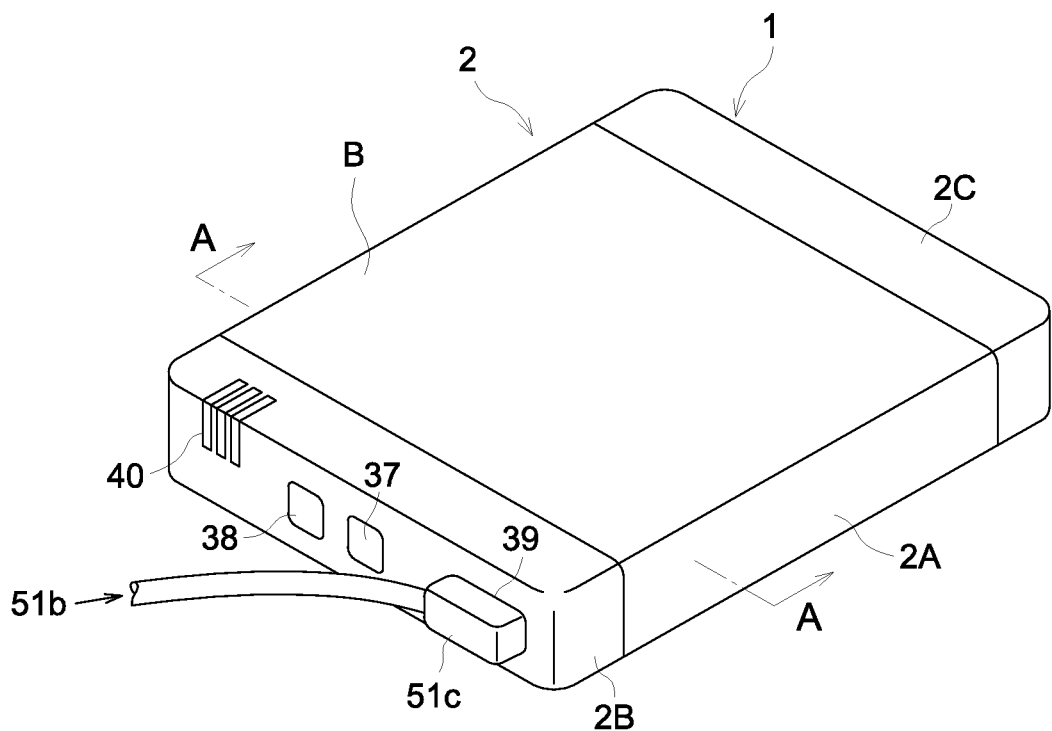
FIG. 11 is an external perspective view showing the connection between the connector of the radiographic imaging device and that of the notification device.

As described above, before the radiographic imaging device 1 is mounted on the bucky device 51, the connector 51c of the notification device 51b is connected to the connector 39, as shown in FIG. 11, and the information such as the bucky ID information as the identification information of the bucky device 51 is sent from the notification device 51b. Then the control device 22 of the radiographic imaging device 1 sends both the bucky ID and the cassette ID of the radiographic imaging device 1 to the console C.

The connector 51c of the notification device 51b is removed when the radiographic imaging device 1 is mounted on the bucky device 51. However, it is also possible to adopt such a structure that the radiographic imaging device 1 is mounted on the bucky device 51 with the connector 51c connected to the connector 39 if this is possible.

If the radiation generator 52 related to the bucky device associated with the notification device 51b has not yet started when the connector 39 of the radiographic imaging device 1 is connected with the connector 51c of the notification device 51b, the radiation generator 52 automatically starts up when connection has been completed, and the position of the generator and direction of irradiation are adjusted in conformity to the bucky device 51.

As shown in FIG. 10, in the present embodiment, the radiographing chamber Ra is provided with a bucky device 51A for image capturing at a standing position and a bucky device 51B for image capturing at a recumbent position. However, the present invention is also applicable when the radiographing chamber Ra is provided with only one bucky device 51, i.e., a bucky device 51A for image capturing at a standing position, for example.

In the present embodiment, by changing the position or direction of irradiation of one of the radiation generators 52, i.e., the radiation generator 52A, radiation can be applied to the radiographic imaging device 1 mounted on the bucky device 51A for image capturing at a standing position or the bucky device 51B for image capturing at a recumbent position, and radiographic image capturing operation can be performed.

The present embodiment also includes a portable radiation generator not associated with the bucky device 51A for image capturing at a standing position or bucky device 51B for image capturing at a recumbent position. The portable radiation generator 52B can be brought to any desired position in the radiographing chamber Ra and radiation can be applied in any desired direction. Radiation can be applied at an appropriate distance or in appropriate direction while the radiographic imaging device 1 is applied to the portion of the patient's body as a subject independently (without the device mounted on the bucky device 51), or the radiographic imaging device 1 is placed between the patient body and the bucky device 51B for image capturing at a recumbent position or the bed (not illustrated).

The radiographing chamber Ra is shielded with lead or the like to ensure that the radiation applied in the radiographing chamber Ra will not leak to the outside. Thus, even if an attempt is made to send or receive information from the radiographic imaging device 1 through the antenna device 41 in the radiographing chamber Ra, such information cannot be sent directly. Thus, in the present embodiment, a base station (wireless access point) 54 equipped with a wireless antenna 53 is provided to relay the communication when wireless communication is carried out between the radiographic imaging device 1 and console C.

When relaying the communication, the base station 54 adds the information on its own base station ID to the information to be relayed. By checking the base station ID of the base station 54 attached to the information, it is possible to identify one of the radiographing chambers R (R1 through R4) from which the information has been sent. To be more specific, the base station 54 is installed in each of the radiographing chambers R. If the base station ID of the base station 54 has been sent, the receiver can identify the information sent from the radiographing chamber R where this base station 54 is installed. The base station ID of the base station 54 is equivalent to the identification information of the radiographing chamber R.

Further, the base station 54 is connected with the cradle 55. The cradle 55 is normally used to store or recharge the radiographic imaging device 1. In the embodiment of the present invention, however, the cradle 55 is used to register the radiographic imaging device 1 having been inserted.

Figure 12:
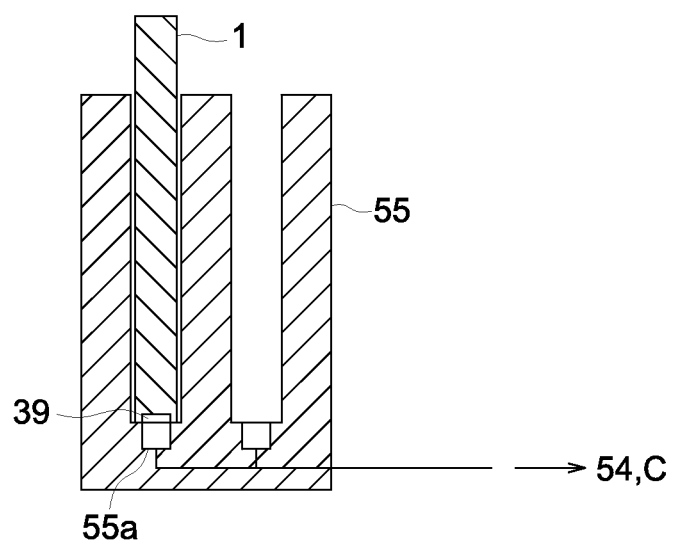
FIG. 12 is a cross sectional view illustrating insertion of the radiographic imaging device into a cradle and connection between connectors.

To put it more specifically, in the present embodiment, the radiographic imaging device 1 is brought into the radiographing chamber Ra, and is inserted into the cradle 55, as shown in FIG. 12. When the connector 39 of the radiographic imaging device 1 is brought in contact with the connector 55a at the inlet of the cradle 55, the cradle 55 as a registration device reads the cassette ID as the identification information of the radiographic imaging device 1, and sends this information to the corresponding console C or management device S (FIGS. 1 and 2) through the base station 54.

FIG. 12 shows a cradle 55 equipped with two inlets in which the radiographic imaging device 1 is inserted. The cradle 55 can be provided with only one inlet or three more inlets. The cradle 55 can be designed to recharge the radiographic imaging device 1. The cradle 55 can be installed in either the radiographing chamber Ra or anteroom Rb. When the cradle 55 is to be installed in the radiographing chamber Ra, the cradle 55 is placed in a position not reached by the radiation applied from the radiation generator 52, i.e., in a corner of the room, for example.

The anteroom Rb contains an operation console 57 for controlling irradiation, that is equipped with a switching device 56 to give instructions to start irradiation of the radiation generator 52. The operation console 57 or radiographing chamber Ra can be provided with a display device such as a monitor to display a list of radiographing order information sent from the console C, as will be described later, although not illustrated in FIG. 10.

The console C (FIGS. 1 and 2) is formed of a computer where an unillustrated CPU, ROM, RAM, input/output interface and others are connected with a bus. The ROM stores a prescribed program. The console C reads out the required program and unfolds it on the work area of the RAM, whereby various forms of processing are executed in conformity to the program.

The console C has a display section Ca composed of a CRT (Cathode Ray Tube), LCD (Liquid Crystal Display) and others, and is further connected with input device such as a keyboard and mouse (not illustrated). The console C is connected with a storage device Cb made of a hard disk and others. The storage device Cb stores a table associated with the cassette ID of the radiographic imaging device 1 that can be used for radiographing in each of the radiographing chambers R, information on the type, size or resolution of a scintillator.

The storage device Cb stores a table that associates the radiographing chamber ID as identification of the radiographing chamber R with the base station ID of the base station 54 installed in the radiographing chamber R in advance. Upon receipt of the information on image data or others sent through the base station 54, the console C refers to the table and figures out the radiographing chamber ID of the radiographing chamber R associated with the base station ID of the base station 54, thereby determining that this information is the information sent from the figured-out radiographing chamber R.

As shown in FIGS. 1 and 2, consoles C (C1 through C3) are connected with the radiographing chambers R (R1 through R4) respectively in a prescribed manner (for FIG. 1) or via the network N (for FIG. 2). To be more specific, the consoles C (C1 through C3) are connected with the base station 54 or operation consoles 57 (not illustrated in FIG. 1 or 2, see FIG. 10) of the radiographing chambers R (R1 through R4) in a prescribed manner or via the network N.

As will be described later, the console C ensures that the radiographing order information indicating the details of the radiographing operations conducted in a prescribed radiographing chamber R is managed in units of the radiographing chamber. The console C and radiographing chamber R are associated with each other in such a way that, when the radiographing order information is sent to the operation console 57 of the radiographing chamber R from the console C, the radiographing conditions for the tube current or tube voltage at the time of radiographing operation are automatically set on the radiation generator 52.

Prior to radiographing, list-formed radiographing order information of radiographing having been generated by the HIS or RIS connected to the network N is sent to each console C. The operator uses any one of the consoles C to select from this list, the radiographing order information for radiographing to be performed in each radiographing chamber.

In the present embodiment, the radiographing order information includes a "patient ID" P2, "patient name" P3, "sex" P4, "age" P5, and "diagnosis department" P6 as the patient information, and "radiographed body part" P7, and "radiographing direction" P8 as the radiographing information, as shown in FIG. 13. According to the order of receiving the radiographing order, the "radiographing order ID" P1 is automatically assigned to the radiographing order information.

The contents of the patient information and radiographing conditions to be written into the radiographing order information are not restricted to the aforementioned. For example, information on the date of birth of a patient, the number of diagnosis, dosage of radiation, and physical constitution (whether fat or lean body) can be included. Desired details of patient information can be set.

On acquisition of the radiographing order information from the HIS or RIS, a list of radiographing order information is displayed on the display section Ca of the console C as selection screen H1, as shown in FIG. 14. In the present embodiment, the selection screen H1 contains a radiographing order information display area h11 for showing the list of radiographing order information. Selection buttons h12 associated with the radiographing order information for selecting the radiographing order information scheduled in the desired radiographing chamber R are provided on the left of the radiographing order information display area h11. Further, the determination button h13 and return button h14 are provided below the radiographing order information display area h11.

The operator clicks on the selection button h12 to select one or more items of radiographing order information for radiographing to be carried out in a desired radiographing chamber R, and clicks on the determination button h13. The operator selects a desired radiographing chamber R on the screen for selection of the radiographing chambers R1 through R4 displayed after having clicked on the determination button h13, although not illustrated. When the radiographing order information and a desired radiographing chamber R have been selected, a list of the selected radiographing order information is associated with the radiographing chamber ID of the desired radiographing chamber R and is stored in the storage device Cb.

At the same time, a list of the radiographing order information selected is sent from the console C operated by the operator to the operation console 57 of the desired radiographing chamber R. As described above, when the list of the radiographing order information is sent to the desired radiographing chamber R from the console C, the console C and desired radiographing chamber R are associated with each other.

It is also possible to adopt such a structure that, before the list of radiographing order information is created, a desired radiographing chamber R is selected, and the console and the desired radiographing chamber R are associated with each other. Further, if the console C and radiographing chamber R are associated in a one-to-one relation in advance, as in the case of the console C1 and radiographing chamber R1 of FIG. 1, it is possible to omit a display on the screen for selecting the radiographing chamber R after the operator has clicked on the determination button h13.

When the radiographing chamber R has been selected on the screen for selection of the radiographing chamber R, the console C acquires the information on the radiographic imaging device 1 currently present in the desired radiographing chamber R from the management device S (FIGS. 1 and 2). Various forms of icons are displayed on the display section Ca, as illustrated in FIGS. 15 and 16.

Figure 15:
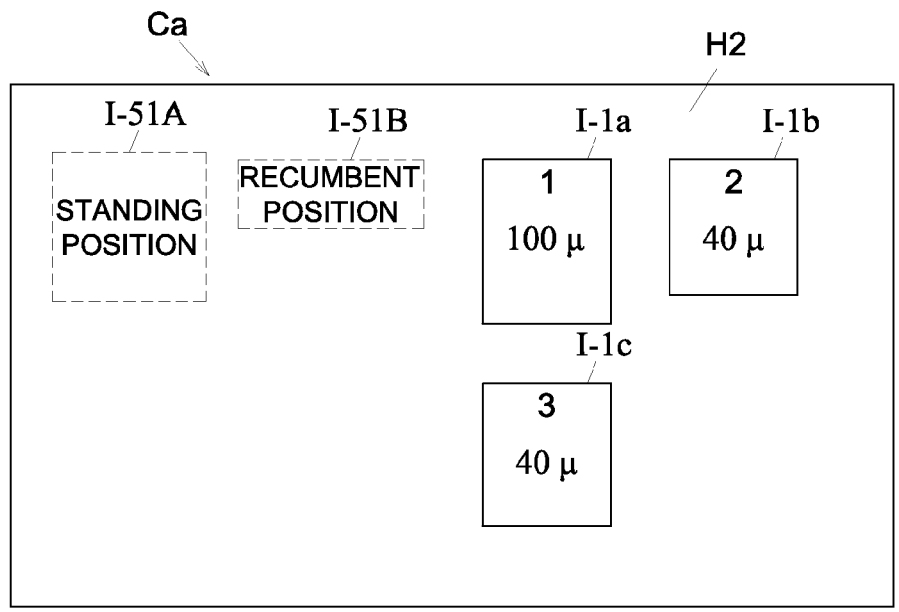
FIG. 15 is a drawing showing an example of an icon displayed on the selection screen of the console, corresponding to the bucky device and the radiographic imaging device.
Figure 16:
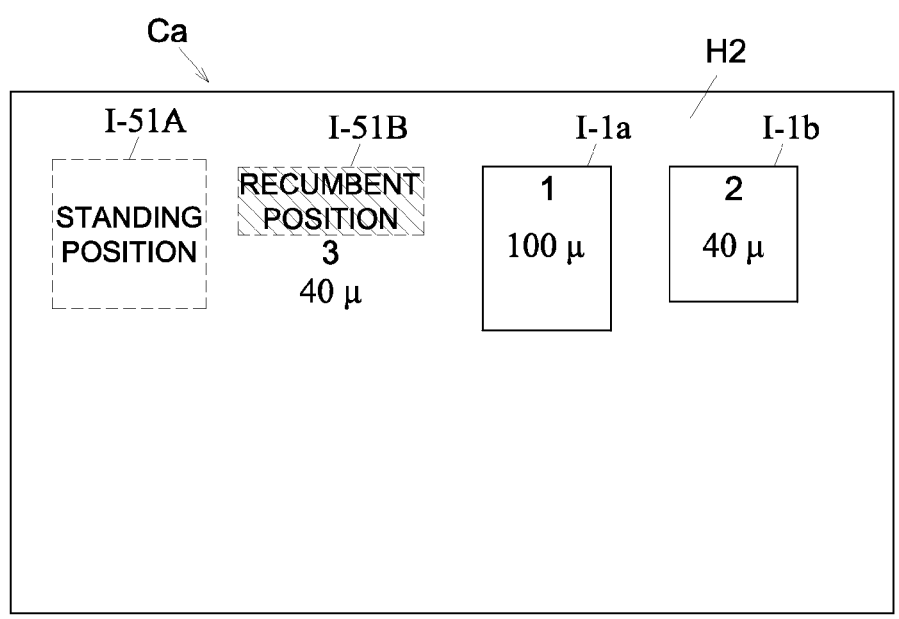
FIG. 16 is a drawing showing an example of an icon displayed on the selection screen of the console, corresponding to the bucky device and the radiographic imaging device.

To put it more specifically, in the present embodiment, icons I-51A and I-51B respectively associated with the bucky device 51A for image capturing at a standing position and bucky device 51B for image capturing at a recumbent position are displayed on the left part in the selection screen H2, in such a way that the indications of "standing position" and "recumbent position" are enclosed by a rectangular frame line, as shown in FIGS. 15 and 16. Icons I-1a through I-1c corresponding to the radiographic imaging device 1 currently present in the radiographing chamber Ra are displayed on the right part in the selection screen H2. Numbers 1 through 3 are indicated in the rectangular frame lines of the icons I-1a through I-1c.

In the present embodiment, if the radiographic imaging device 1 is not mounted on the bucky device 51, the frame line of the icon I associated with the bucky device 51 is displayed by a broken line on the console C ("standing position" I-51A and "recumbent position" I-51B of FIG. 15 and "standing position" I-51A of FIG. 16). This indicates that the bucky device 51 is not loaded with the radiographic imaging device 1.

If the radiographic imaging device 1 is mounted on the bucky device 51 (more accurately, if the connector 39 of the radiographic imaging device 1 in the radiographing chamber R is connected with the connector 51c of the notification device 51b), the frame line of the icon I corresponding to the bucky device 51 is displayed by a solid line on the console C, and the description inside the frame line is displayed in a prescribed color ("recumbent position" I-51B of FIG. 16). This icon indicates that the bucky device 51 is loaded with the radiographic imaging device 1. In FIG. 16, the number or resolution of the radiographic imaging device 1 loaded on the bucky device 51B for image capturing at a recumbent position is displayed in the vicinity of the "recumbent position" I-51B.

In the present embodiment, for example, if the icon I-1 corresponding to the radiographic imaging device 1 shown in FIGS. 15 and 16 is clicked, the radiographic imaging device 1 can be selected as the device to be used from now Similarly, when the selector switch 38 of the radiographic imaging device 1 is pressed, the radiographic imaging device 1 can also be selected as the device to be used from now, as described above.

The console C has the function where the icon I-1 associated with the radiographic imaging device 1 is newly displayed on the selection screen H2 of the display section Ca of the console C, if the cassette ID as the identification information of the radiographic imaging device 1 has been notified from the cradle 55 as a registration device of the radiographing chamber R, for example, when the radiographic imaging device 1 has been newly brought into the associated radiographing chamber R.

Mounting of the No. 3 radiographic imaging device 1 on the bucky device 51B for image capturing at a recumbent position can be designated in advance, for example, by clicking on the icon I-51B associated with the bucky device 51B for image capturing at a recumbent position after clicking on the icon I-1c associated with the No. 3 radiographic imaging device 1 shown in FIG. 15 or by dragging and dropping the icon I-1c on the icon I-51B. This operation procedure converts the selection screen H2 from the state of FIG. 15 to the state of FIG. 16.

In the present invention, when the radiographic imaging device 1 to be mounted on the bucky device 51 is specified in advance on the selection screen H2 of the console C, the signal denoting selection of the bucky device 51 for a selected radiographing chamber R is sent to the operation console 57 of the radiographing chamber R from the console C.

Upon receipt of the signal, the operation console 57 starts the radiation generator 52A (FIG. 10), moves the radiation generator 52A and adjusts the direction of irradiation so that radiation can be appropriately applied to the specified bucky device 51 (e.g, bucky device 51B for image capturing at a recumbent position) based on the received signal. Further, the operation console 57 adjusts a diaphragm (not illustrated) so that radiation will be applied within a prescribed range of the bucky device 51, and adjusts the radiation generator 52 so that an appropriate dosage of radiation will be applied.

This structure allows the radiation generator 52 to be started in advance by the operation of the console C, and permits the radiographing operation to be started immediately when the operator has moved into the radiographing chamber R. It is possible to arrange the structure in such a way that an audio signal will be issued to give an alert, if the operator having moved into the radiographing chamber R has started the radiographing operation without mounting the radiographic imaging device 1 on the bucky device 51, although the instruction has been made on the selection screen H2 of the console C to mount the radiographic imaging device 1 on the bucky device 51.

It is also possible to make such arrangements that, if there is a portable radiation generator 52B (FIG. 10) in the radiographing chamber R, the icon I associated therewith is displayed on the selection screen H2 of the console C, and the portable radiation generator 52B is started by the operation of the console C, similarly to the case of the radiation generator 52A, although this is not illustrated in FIGS. 15 and 16.

The above description is based on the assumption that the operator operates the console C prior to radiographing operation. When the selection signal indicating the selection of itself is sent from the radiographic imaging device 1, for example, by depression of the selector switch 38 of the radiographic imaging device 1 after the operator has moved into the radiographing chamber R, the console C indicates that the radiographic imaging device 1 has been selected, for example, by displaying the colored icon I-1 corresponding to the radiographic imaging device 1 on the selection screen H2.

As described above, the connector 51c of the notification device 51b is connected to the connector 39 of the radiographic imaging device 1 in the radiographing chamber R by the operator (FIG. 11). The bucky device ID and cassette ID of the radiographic imaging device 1 are sent to the console C from the radiographic imaging device 1 through the antenna device 41. In this case, when the No. 3 radiographic imaging device 1 of FIG. 15 is connected with the notification device 51b corresponding to the bucky device 51B for image capturing at a recumbent position, the console C switches the selection screen H2 from the state of FIG. 15 to the state shown in FIG. 16 indicating that the radiographic imaging device 1 has been mounted on the bucky device 51B for image capturing at a recumbent position.

When radiographing has been completed in the associated radiographing chamber R based on the radiographing order information, such data as image data or dark readings is sent to the console C from the radiographic imaging device 1 through the antenna device 41 and base station 54. Then the console C associates the radiographing order information with the image data or dark readings captured in conformity to the radiographing order information, and stores the same in the storage device Cb.

Image processing is performed on the console C in conformity to the image data or dark readings, and the final image data according to the radiographing order information is generated. When this final image data has been generated, the console C associates the final image data with the radiographing order information and stores the same in the storage device Cb.

In the embodiment of the present invention, the radiographic imaging device 1 is brought, for example, from the radiographing chamber R1 to the radiographing chamber R2, and the radiographic imaging device 1 is inserted into the cradle 55 as the registration device of the radiographing chamber R2. When the cassette ID as the identification information of the radiographic imaging device 1 is notified to the management device S or console C from the cradle 55, the console C associated with the radiographing chamber R2 ensures that the icon I-1 associated with the radiographic imaging device 1 is newly displayed on the selection screen H2, and the console C associated with the radiographing chamber R1 ensures that the icon I-1 associated with the radiographic imaging device 1 is deleted from the selection screen H2. This will be described in detail with reference to the management device S to be described below.

The management device S (FIGS. 1 and 2) is formed of a computer where an unillustrated CPU, ROM, RAM, input/output interface and others are connected with a bus. The management device S is connected with a storage device Sa made of a hard disk and others. The storage device Sa stores the table where the radiographing chamber ID as the identification information of the radiographing chamber R is associated with the base station ID of the base station 54 installed in the radiographing chamber R.

Upon receipt of various forms of information sent through the base station 54 via the console C in the system shown in FIG. 1 or via the network N in the system of FIG. 2, the management device S refers to the table and figures out the radiographing chamber ID of the radiographing chamber R associated with the base station ID of the base station 54 attached to the information, thereby determining that this information is the one sent from the figured-out radiographing chamber R.

The management device S associates the cassette ID as the identification information of the radiographic imaging device 1 with the radiographing chamber ID as the identification information of the radiographing chamber R, and manages to understand the location of the radiographic imaging device 1 among the radiographing chambers R1 through R4.

To put it more specifically, the radiographic imaging device 1 is brought into the radiographing chamber R and is inserted into the cradle 55 as the registration device. Upon receipt of the cassette ID as the identification information of the radiographic imaging device 1 sent from the cradle 55 through the base station 54, together with the base station ID of the base station 54, the management device S figures out the radiographing chamber ID of the radiographing chamber R associated with the base station ID of the base station 54 and associates the radiographing chamber ID with the cassette ID of the radiographic imaging device 1 and stores the same in the storage device Sa.

In this case, when the radiographic imaging device 1 has been newly introduced into this radiographic imaging system 100, the radiographing chamber ID is associated with the cassette ID of the newly introduced radiographic imaging device 1 in the above-mentioned manner, and is stored in the storage device Sa. However, when the cassette ID of the radiographic imaging device 1 has already been used in the radiographic imaging system 100 and had been associated with the radiographing chamber ID of another radiographing chamber R, the management device S deletes the previous association between the radiographing chamber ID of the radiographing chamber R and cassette ID of the radiographic imaging device 1 from the storage device Sa.

As described above, if the cassette ID of the radiographic imaging device 1 has been sent from the cradle 55, for example, when the radiographic imaging device 1 is newly brought into the radiographing chamber R, the console C associated with the radiographing chamber R allows the icon I-1 corresponding to the radiographic imaging device 1 to be newly displayed on the selection screen H2.

However, the console C associated with another radiographing chamber R where the radiographic imaging device 1 was previously located cannot identify the radiographic imaging device 1 having been brought out of the radiographing chamber R. Thus, although the radiographic imaging device 1 is no longer present in the radiographing chamber R, the icon I-1 corresponding to the radiographic imaging device 1 remains displayed on the selection screen H2 of the console C associated with the radiographing chamber R.

Under such conditions, for example, the icon I-1 corresponding to the radiographic imaging device 1 already removed from the radiographing chamber R may be put into the icon I-51 corresponding to the bucky device 51 (i.e., I1-51A or I-51B in the present embodiment, applicable in the following description), for example, by a drag-and-drop operation on the selection screen H2 of the console C, and an instruction may be given in such a way that the radiographic imaging device 1 should be loaded, for example, on the bucky device 51B for image capturing at a recumbent position. If this occurs, the radiation generator 52A will be started by the console C so as to be able to apply radiation to the bucky device 51. This may result in unwanted waste of power consumption, and incorrect irradiation may take place.

To solve this problem, if the cassette ID of the radiographic imaging device 1 notified by the cradle 55 of the radiographing chamber R has been previously associated with the radiographing chamber ID of another radiographing chamber R, the management device S deletes the association between the radiographing chamber ID of the other radiographing chamber R and the cassette ID of the radiographic imaging device 1 in the storage device Sa. At the same time, the management device S sends the cassette ID of the radiographic imaging device 1 together with the deletion signal to the console C associated with another radiographing chamber R. Then the console C deletes the icon I-1 corresponding to the cassette ID of the radiographic imaging device 1 from the selection screen H2.

To be more specific, assume that icons I-a through I-c corresponding to the radiographic imaging device 1 are displayed on the selection screen H2 of the display section Ca of the console C, as shown in FIG. 15. Then if the No. 3 radiographic imaging device 1, for example, is brought from the radiographing chamber R to another radiographing chamber R, the icon I-1c corresponding to the No. 3 radiographic imaging device 1 will be newly displayed on the selection screen H2 of the console C associated with the radiographing chamber R. The icon I-1c corresponding to the No. 3 radiographic imaging device 1 will be deleted from the selection screen H2 of the original console C, as shown in FIG. 17.

Figure 17:
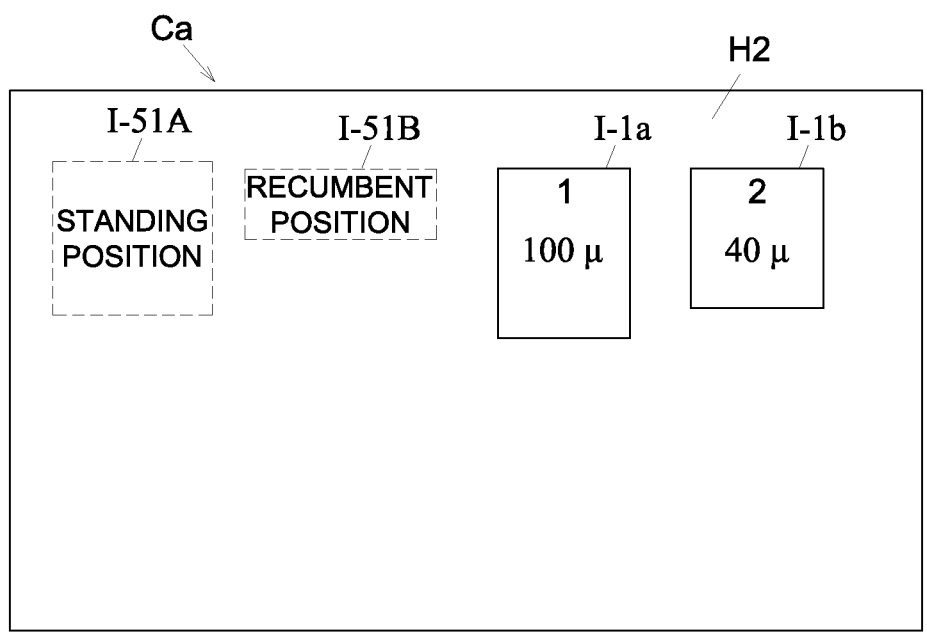
FIG. 17 is a drawing illustrating that the icon corresponding to the radiographic imaging device of number 3 is deleted from the selection screen of FIG. 15.

Further, even when display is given in such a way that the No. 3 radiographic imaging device 1 is loaded, for example, on the bucky device 51B for image capturing at a recumbent position, as shown in FIG. 16, if the No. 3 radiographic imaging device 1 is brought from the radiographing chamber R to another radiographing chamber R and is registered on the cradle 55, the indication (i.e., solid line of the frame line and coloring of the icon I-51B) showing the radiographic imaging device 1 being loaded thereon is deleted from the icon I-51B of the bucky device 51B for image capturing at a recumbent position on which the No. 3 radiographic imaging device 1 is loaded, on the selection screen H2 of the original console C, as shown in FIG. 17. The icon I-52B corresponding to the bucky device 51B for image capturing at a recumbent position goes back to the original broken line (i.e., the state where the radiographic imaging device 1 is not loaded).

When the aforementioned structure is adopted, in the console C corresponding to the radiographing chamber R into which the radiographic imaging device 1 is brought to be inserted into the cradle 55, the icon I-1 corresponding to the radiographic imaging device 1 is newly displayed on the selection screen H2 thereof, and the icon I-1 corresponding to the radiographic imaging device 1 is deleted from the selection screen H2 of the console corresponding to the radiographing chamber R from which the radiographic imaging device 1 has been removed.

When a deletion signal and cassette ID of the radiographic imaging device 1 is sent to the original console C from the management device S, the selection screen H2 may not be displayed on the display section Ca of the original console C in some cases. In such cases, upon receipt of the deletion signal, the original console C ensures that the information of the icon I-1 corresponding to the radiographic imaging device 1 is deleted from its own memory where the information on the contents to be displayed on the selection screen H2 is temporarily stored. This arrangement ensures that the icon I-1 corresponding to the radiographic imaging device 1 is not displayed on the selection screen H2, when the display of the selection screen H2 is instructed again.

The following describes the operation of the radiographic imaging system 100 in the present embodiment.

Prior to starting the radiographing operation, the operator such as a radiographing technician operates the console C2 of FIG. 1, for example, and acquires the radiographing order information for radiographing from the HIS or RIS. In the display section Ca of the console C, a list of the list-formed radiographing order information is displayed on the selection screen H1, as shown in FIG. 14.

The operator clicks on the selection button h12 to select one or more items of radiographing order information for radiographing to be carried out in a desired radiographing chamber R, and clicks on the determination button h13. The operator then selects a desired radiographing chamber R2, for example, on the screen displayed next. When the desired radiographing chamber R2 has been selected, the console C2 associates the selected list of radiographing order information with the radiographing chamber ID of the desired radiographing chamber R2, and stores the same in the storage device Cb. The console C2 then sends the list of the selected radiographing order information to the operation console 57 of the desired radiographing chamber R2. This is how the console C2 and desired radiographing chamber R2 are associated with each other.

Then the console C2 obtains from the management device S the information on the radiographic imaging device 1 currently present in the desired radiographing chamber R2. Each icon I of the radiographic imaging device 1 is displayed on the selection screen H2 of the display section Ca, for example, as shown in FIG. 15.

The operator clicks on the icon I-1 corresponding to the radiographic imaging device 1 and selects this radiographic imaging device 1 as the radiographic imaging device to be used from now Alternatively, the icon I-1 corresponding to a prescribed radiographic imaging device 1 is placed on the icon I-51 corresponding to the bucky device 51 by a drag-and-drop operation. This procedure allows the operator to give an instruction in advance to mount the radiographic imaging device 1 on the bucky device 51, as described above.

If an instruction is given in advance to mount the radiographic imaging device 1 on the bucky device 51, this signal is sent to the operation console 57 of the radiographing chamber R2. Upon receipt of this signal, the operation console 57 starts the radiation generator 52A, moves the radiation generator 52A, adjusts the direction of irradiation or adjusts the diaphragm or dosage of radiation for applying radiation to the specified bucky device 51.

As described above, when the radiographic imaging device 1 to be used is already present in the desired radiographing chamber R2, there is no need of bringing the radiographic imaging device 1 into the desired radiographing chamber R2. However, if the icon I-1 corresponding to the radiographic imaging device 1 to be used is not displayed, and the radiographic imaging device 1 to be used is not present in the radiographing chamber R2, the operator brings the desired radiographic imaging device 1 into the radiographing chamber R2 after completing a series of operations prior to radiographing operation on the console C2.

When the operator has inserted the radiographic imaging device 1 into the cradle 55 of the radiographing chamber R2, the connector 39 of the radiographic imaging device 1 and the connector 55a of the cradle 55 are connected, as shown in FIG. 12, and the cassette ID as the identification information of the radiographic imaging device 1 is read out. Then the cassette ID is sent to the base station 54 from the cradle 55.

Upon receipt of the cassette ID from the cradle 55, the base station 54 adds the base station ID of its own and sends this information to the console C2 or management device S.

Upon receipt of the cassette ID and base station ID of the base station 54, the console C2 refers to the table where the radiographing chamber ID as the identification information of the radiographing chamber R and the base station ID of the base station 54 are associated, and makes sure that this cassette ID is the one sent from the desired radiographing chamber R. Then the icon I corresponding to this radiographic imaging device 1 is newly displayed on the selection screen H2 of the display section Ca.

Similarly, upon receipt of the cassette ID and base station ID of the base station 54, similarly the management device S refers to the table where the radiographing chamber ID as the identification information of the radiographing chamber R and the base station ID of the base station 54 are associated, and figures out the radiographing chamber ID of the radiographing chamber R2 associated with the base station ID of the base station 54. The management device S then associates the radiographing chamber ID with the cassette ID of the radiographic imaging device 1 and stores the same in the storage device Sa, thereby managing to understand the location of the radiographic imaging device 1 among the radiographing chambers R1 through R4.

As described above, when the selector switch 38 of the radiographic imaging device 1 has been pressed by the operator after the radiographic imaging device 1 has been inserted into the cradle 55 of the radiographing chamber R2 and has been registered, a selection signal is sent from the antenna device 41 of the radiographic imaging device 1. This selection signal is sent to the console C2 through the base station 54.

The console C2 indicates that the radiographic imaging device 1 has been select, for example, by adding color to the icon I-1 corresponding to the radiographic imaging device 1 displayed on the selection screen H2.

When the connector 51c of the notification device 51b is connected to the connector 39 of the radiographic imaging device 1 by the operator in the radiographing chamber R2, the control device 22 of the radiographic imaging device 1 acquires the bucky ID of the bucky device 51 corresponding to the notification device 51b notified by the notification device 51b, and sends the bucky ID and cassette ID of the radiographic imaging device 1 to the console C2 through the antenna device 41.

Upon receipt of the bucky ID and cassette ID, the console C2 changes the display from FIG. 15 to FIG. 16, and shows that the radiographic imaging device 1 has been mounted on the bucky device 51.

When the radiographing operation in conformity to the radiographing order information has been terminated in the associated radiographing chamber R2, and the image data or dark readings have been sent from the radiographic imaging device 1 through the antenna device 41 or base station 54, the console C2 associates the image data captured in conformity to the radiographing order information or dark readings with the radiographing order information, and stores the same in the storage device Cb.

After that, image processing is performed based on the image data or dark readings on the console C2. When the final image data has been generated based on the radiographing order information, the console C2 associates this final image data with the radiographing order information and stores the same in the storage device Cb, as described above.

For example, when another operator wishes that the radiographic imaging device 1 used in the radiographing chamber R2 should be used for radiographing in the radiographing chamber R1, this radiographic imaging device 1 is brought into the radiographing chamber R1 from the radiographing chamber R2. In this case, this operator operates the console C1 to select new radiographing order information or selects the radiographing chamber R1 as the desired radiographing chamber R. After completing such processing prior to radiographing, the operator brings the radiographic imaging device 1 from the radiographing chamber R2 into the radiographing chamber R1.

When the radiographic imaging device 1 has been inserted into the cradle 55 of the radiographing camber R1 by the operator, the cassette ID as the identification information of the radiographic imaging device 1 is sent to the console C1 or management device S from the cradle 55 through the base station 54 of the radiographing chamber R1. Similarly to the aforementioned case, the console C1 allows the icon I-1 corresponding to the radiographic imaging device 1 to be displayed newly on the selection screen H2 of the display section Ca.

Upon receipt of the cassette ID and the base station ID of the base station 54, the management device S refers to the table where the radiographing chamber ID as the identification information of the radiographing chamber R and the base station ID of the base station 54 are associated, and figures out the radiographing chamber ID as the identification information of the radiographing chamber R1 associated with the base station ID of the base station 54. The management device S then associates the radiographing chamber ID with the cassette ID of the radiographic imaging device 1 and stores the same in the storage device Sa.

In this case, the management device S deletes the association between the radiographing chamber ID of the radiographing chamber R2 and the cassette ID of the radiographic imaging device 1 in the storage device Sa, since the cassette ID of the radiographic imaging device 1 having been sent had been previously associated with the radiographing chamber ID of another radiographing chamber R2.

The management device S sends the deletion signal and the cassette ID of the radiographic imaging device 1 to the console C2 associated with the radiographing chamber R2, and allows the console C2 to delete the icon I-1 corresponding to the cassette ID of the radiographic imaging device 1 from the selection screen H2.

As described above, the radiographic imaging device 1 is inserted into the cradle 55 of the radiographing chamber R1 and the radiographic imaging device 1 is newly registered. This permits the icon I-1 corresponding to the radiographic imaging device 1 to be newly displayed on the selection screen H2 of the console C1, and ensures the icon I-1 corresponding to the radiographic imaging device 1 to be deleted from the selection screen H2 of the console C2.

When the radiographic imaging device 1 is mounted on the bucky device 51 in the original radiographing chamber R2, the icon is displayed on the selection screen H2 of the console C2, as shown in FIG. 16, in such a way that the radiographic imaging device 1 is mounted on the bucky device 51. When the radiographic imaging device 1 is newly registered by the cradle 55 of the radiographing chamber R1, the aforementioned displayed icon on the selection screen H2 of the console C2 is deleted by the aforementioned processing of the management device S, and the display of the icon of FIG. 16, for example, is switched over to the display of FIG. 17.

As described above, according to the radiographic imaging system 100 of the present embodiment, upon receipt of the cassette ID as the identification information of the radiographic imaging device 1 from the cradle 55 as a registration device of the radiographing chamber R, the management device S associates the radiographing chamber ID as the identification information of the radiographing chamber R with the cassette ID of the radiographic imaging device 1, and stores the same. Further, when the cassette ID of the radiographic imaging device 1 has been associated with the radiographing chamber ID of another radiographing chamber R, the management device S detects the association with the radiographing chamber ID of the other radiographing chamber R and the cassette ID of the radiographic imaging device 1.

In the radiographic imaging system 100 equipped with a plurality of radiographing chambers R, this structure ensures the management device S to provide accurate management of the location of the radiographic imaging device 1 among the radiographing chambers R.

Upon receipt of the cassette ID of the radiographic imaging device 1 from the cradle 55 of the radiographing chamber R, the console C allows the icon I-1 corresponding to the radiographic imaging device 1 to be displayed on the selection screen H2. At the same time, upon receipt of the cassette ID of the radiographic imaging device 1 from the cradle 55 of another radiographing chamber R, the management device S deletes the icon I-1 corresponding to the radiographic imaging device 1 from the selection screen H2 of the original console C associated with the original radiographing chamber R where the radiographic imaging device 1 was present.

This structure ensures the icon I-1 corresponding to the radiographic imaging device 1 to be correctly displayed on the selection screen H2 of the console C associated with the radiographing chamber R containing the radiographic imaging device 1. When the radiographic imaging device 1 has been removed from the radiographing chamber R, the icon I-1 corresponding to the radiographic imaging device 1 is automatically deleted by the management device S from the selection screen H2 of the console C associated with the radiographing chamber R.

This structure completely solves the problem of failing to identify the current position of a radiographic imaging device 1, despite the presence of this radiographic imaging device 1 in the radiographing chamber R, or keeping an icon I-1 corresponding to the radiographic imaging device 1 to be displayed on the selection screen H2 of the console C associated with the radiographing chamber R, despite the absence of this radiographic imaging device 1 in the radiographing chamber R. Thus, appropriate operation of the radiographic imaging system 100 is ensured.

As described above, in the present embodiment, the bucky device for the existing CR cassette in the radiographing chamber R is assumed to be used as a bucky device 51. Not only the radiographic imaging device 1 but also the CR cassette can be mounted on the bucky device 51 to perform radiographing operations. In this case, both the radiographic imaging device 1 and CR cassette are present in the radiographing chamber R. It is possible to make such arrangements as to ensure appropriate identification of each of them.

In the present embodiment, bucky devices 51A for image capturing at a standing position and bucky devices 51B for image capturing at a recumbent position are installed in all the radiographing chambers R1 through R4. There is no restriction to the type of bucky devices 51 installed in each room. Only the bucky devices 51A for image capturing at a standing position can be installed in some of the rooms, while only bucky devices 51B for image capturing at a recumbent position can be installed in other rooms. The present invention also applies to such rooms containing different types of bucky devices 51.

Figure 18:
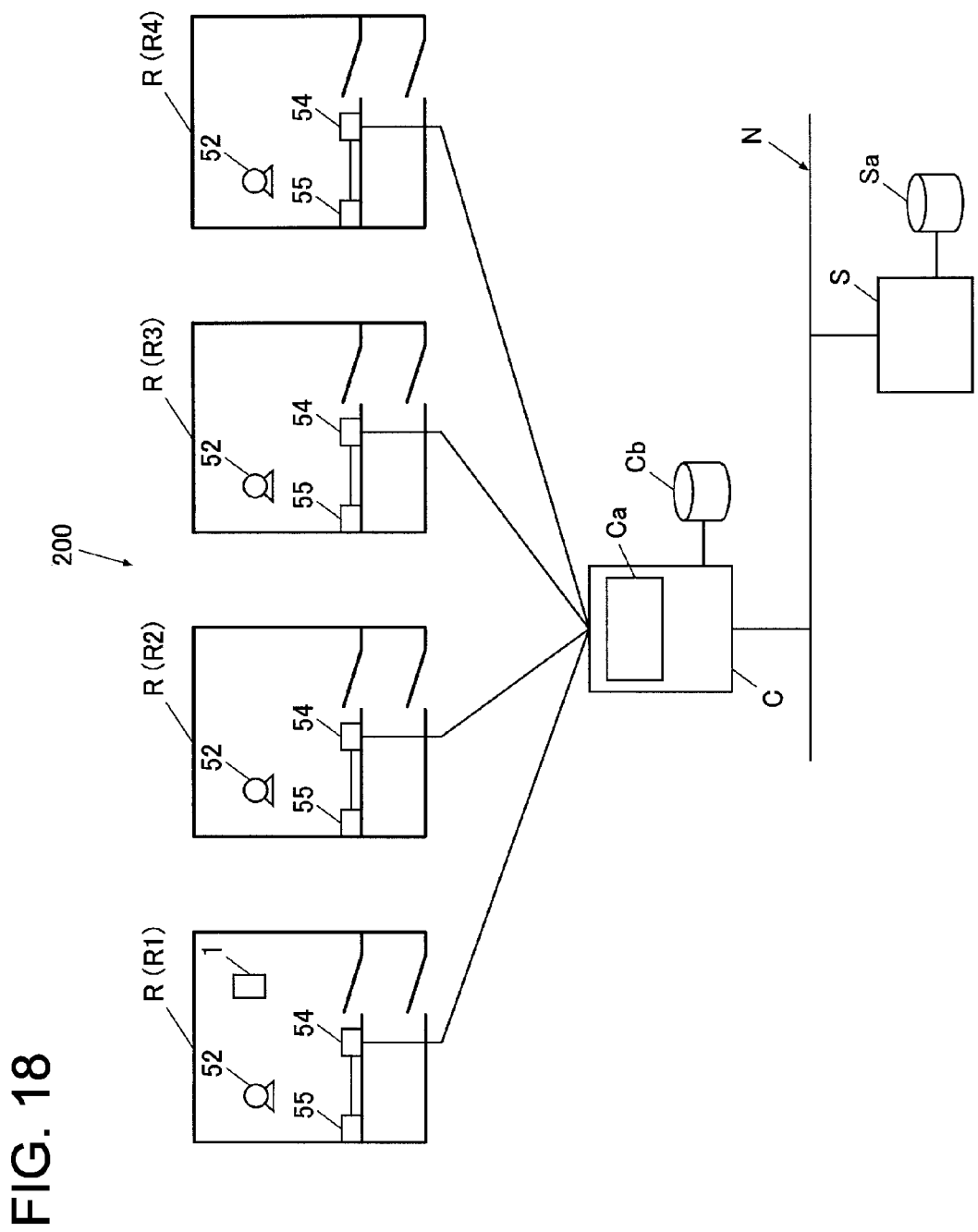
FIG. 18 is a drawing illustrating an overall structure of the radiographic imaging system equipped with only one console.
Figure 19:
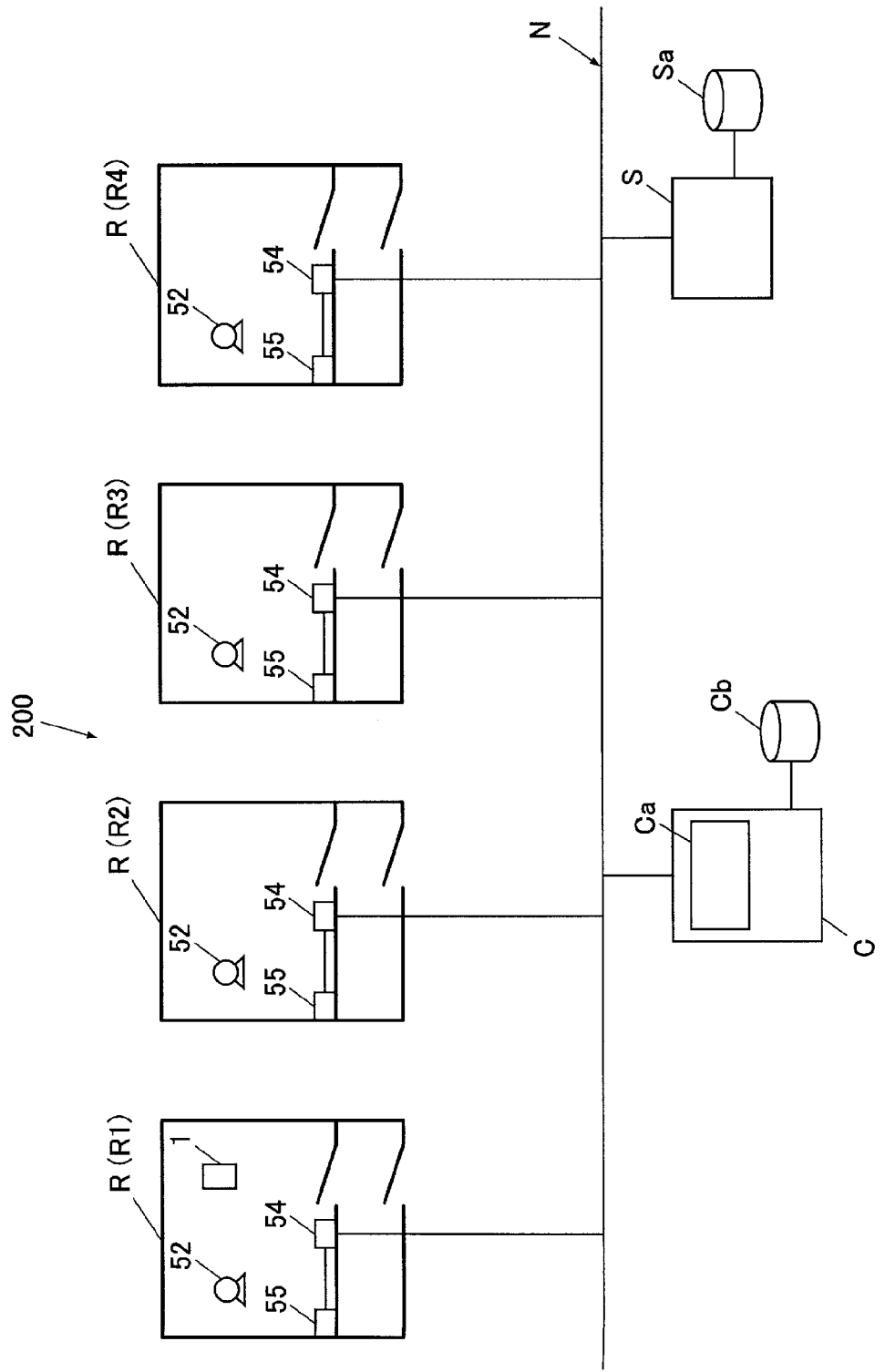
FIG. 19 is a drawing illustrating another overall structure of the radiographic imaging system equipped with only one console.

The present embodiment has been described with reference to the case where the radiographic imaging system 100 contains a plurality of radiographing chambers R (R1 through R4) and a plurality of consoles C (C1 through C3), as shown in FIGS. 1 and 2. The present invention also applies to the radiographic imaging system 200 containing a plurality of radiographing chambers R (R1 through R4) and one console C, as shown in FIGS. 18 and 19.

In this case, for example, when the console C and radiographing chamber R1 are associated with each other, i.e., when the icons I-1 and I-51 respectively corresponding to the radiographic imaging device 1 and bucky device 51 located in the radiographing chamber R1 are displayed on the selection screen H2 of the console C, the radiographic imaging device 1 is brought into the radiographing chamber R2 from the radiographing chamber R1, and the radiographic imaging device 1 is inserted into the cradle 55 as the registration device of the radiographing chamber R2 and is registered. In this case, the management device S deletes the icon I-1 corresponding to the radiographic imaging device 1 from the selection screen H2 of the console C displaying the icons I-1 and I-51 respectively corresponding to the radiographic imaging device 1 and bucky device 51 present in the radiographing chamber R1.

As described above, similarly to the case of the radiographic imaging system 100 of the above embodiment, in the radiographic imaging system 200 containing a plurality of radiographing chambers R (R1 through R4) and one console C, the management device S ensures accurate management to understand the location of the radiographic imaging device 1 in radiographing chambers R. Not only that, the management device S certainly avoids occurrence of failures and provides appropriate operation of the radiographic imaging system 200.

It should be noted that, in the radiographic imaging system 200, integral construction of the console C and management device S can be achieved, for example, when the console C is designed to incorporate the functions of the management device S.

Further, it goes without saying that the present invention is not restricted to the aforementioned embodiments. The present invention can be appropriately modified.

What is claimed is:

1. A radiographic imaging system comprising:
   a portable radiographic imaging device which can be used in common in a plurality of radiographing chambers;
   at least one console which has a display section, and which sets radiographing order information including information on a patient as a subject of radiographing and a condition of radiographing and which associates the radiographing order information with image data captured based on the radiographing order information;
   a management device which associates identification information of the portable radiographic imaging device with identification information of a radiographing chamber, and manages to know where the portable radiographic imaging device is located among the plurality of radiographing chambers; and
   a registration device which is installed in each of the plurality of radiographing chambers and which reads and outputs the identification information of the portable radiographic imaging device,
   wherein the console is associated with one of the plurality of radiographing chambers selectively at a time of radiographing or in advance, and, when the identification information of the portable radiographic imaging device outputted from the registration device provided in the associated one of the plurality of radiographing chambers has been notified to the console, the console causes the display section to display an icon corresponding to the portable radiographic imaging device thereon, and
   wherein the management device, when notified of the identification information of the portable radiographic imaging device outputted from the registration device, stores the identification information of the radiographing chamber provided with the registration device and the identification information of the portable radiographic imaging device after being associated with each other, and, if the identification information of the portable radiographic imaging device has been associated with the identification information of another radiographing chamber, discards the association therebetween and deletes the icon corresponding to the portable radiographic imaging device from the display section of the console associated with the another radiographing chamber.

2. The radiographic imaging system of claim 1,
   wherein the plurality of radiographing chambers include a bucky device which can be loaded with the portable radiographic imaging device, and the bucky device comprises:
   a notification device for notifying the portable radiographic imaging device installed on the bucky device about identification information of the bucky device,
   wherein when having received the identification information of the bucky device from the notification device, the portable radiographic imaging device transmits the identification information of the bucky device together with the identification information of the portable radiographic imaging device to the console, wherein when receiving from the portable radiographic imaging device identification, the information of the bucky device together with the identification information of the portable radiographic imaging device, the console displays an icon indicating that the portable radiographic imaging device has been installed on the bucky device on the display section.

3. The radiographic imaging system of claim 2, further comprising:

at least one radiation generator for emitting radiation in the radiographing chamber, wherein when the portable radiographic imaging device and the notification device are connected with each other, the radiographic imaging system starts the radiation generator which is to be used to emit radiation to the bucky device which corresponds to the notification device.

4. The radiographic imaging system of claim 3, wherein when the bucky device to be provided with the portable radiographic imaging device is designated by operating the icon on the display section, the console starts the radiation generator which is to be used to emit radiation to the bucky device.

* * * * *